(12) United States Patent
Schuppan et al.

(10) Patent No.: US 11,795,213 B2
(45) Date of Patent: Oct. 24, 2023

(54) METHODS AND COMPOSITIONS FOR TREATING CELIAC DISEASE

(71) Applicant: Beth Israel Deaconess Medical Center, Inc., Boston, MA (US)

(72) Inventors: Detlef Schuppan, Mainz (DE); Yvonne Junker, Kiel (DE); Towia Aron Libermann, Chestnut Hill, MA (US); Simon T. Dillon, Danvers, MA (US)

(73) Assignee: Beth Israel Deaconess Medical Center, Inc., Boston, MA (US)

( * ) Notice: Subject to any disclaimer, the term of this patent is extended or adjusted under 35 U.S.C. 154(b) by 0 days.

(21) Appl. No.: 15/666,030

(22) Filed: Aug. 1, 2017

(65) Prior Publication Data

US 2018/0179268 A1    Jun. 28, 2018

Related U.S. Application Data

(63) Continuation of application No. 13/695,349, filed as application No. PCT/US2011/034516 on Apr. 29, 2011, now abandoned.

(60) Provisional application No. 61/330,043, filed on Apr. 30, 2010, provisional application No. 61/417,613, filed on Nov. 29, 2010.

(51) Int. Cl.
*C12N 15/82* (2006.01)
*C07K 16/18* (2006.01)
*C07K 16/16* (2006.01)
*A61K 39/00* (2006.01)

(52) U.S. Cl.
CPC .............. *C07K 16/18* (2013.01); *C07K 16/16* (2013.01); *A61K 2039/505* (2013.01); *C07K 2317/76* (2013.01); *C12N 15/8218* (2013.01); *C12N 15/8245* (2013.01)

(58) Field of Classification Search
None
See application file for complete search history.

(56) References Cited

U.S. PATENT DOCUMENTS

| | | | | |
|---|---|---|---|---|
| 5,789,380 | A * | 8/1998 | Miyazaki | A61K 38/56 514/5.5 |
| 6,190,723 | B1 * | 2/2001 | Buchanan | A21D 2/26 426/656 |
| 2003/0135878 | A1 * | 7/2003 | Cho | A21D 13/064 800/278 |
| 2007/0184049 | A1 | 8/2007 | Fox | |

FOREIGN PATENT DOCUMENTS

WO    WO-2007/056301 A2    5/2007

OTHER PUBLICATIONS

Amano et al. 1998. Biochem J. 330:1229-1234 (Year: 1998).*
Constantin et al. 2009. Int. Arch. Allergy Immunol. 149:181-187 (Year: 2009).*
Kusaba-Nakayama et al. 2000. Food and Chem Toxicol. 38:179-185 (Year: 2000).*
Faris et al. (2008. J. Agric Food Chem 56:7146-7150). (Year: 2008).*
Cakir et al., Crop Sci. 50:S-77-S-84 (2010); doi: 10.2135/cropsci2009.10.0567. Published online Feb. 8, 2010.*
Fu et al., Transgenic Res (2007) 16:689-701. DOI 10.1007/s11248-007-9150-7.*
Tatham, A. S., and P. R. Shewry. "Allergens to wheat and related cereals." Clinical & Experimental Allergy 38.11 (2008): 1712-1726. (Year: 2008).*
Tada, Yuichi, et al. "Reduction of 14-16 kDa allergenic proteins in transgenic rice plants by antisense gene." FEBS letters 391.3 (1996): 341-345. (Year: 1996).*
Gomez et al, 1990, FEBS, 261:85-88.*
Amano et al, 1998, Biochem. J., 330:1229-1234.*
Gil-Humanes et al (2010, PNAS, 39:17023-17028.*
Pastorello et al, 2007, Int Arch Allergy Immunol, 144:10-22.*
Tatham et al, 2008, Clinical and Experimental Allergy, 38:1712-1726.*
Shewry et al, 1984, FEBS Letters, 175:359-363.*
Oda et al (1997, Biochemistry 36:13503-13511.*
Extended European Search Report and Written Opinion for European Patent Application No. 11775619.7, dated Oct. 22, 2013 (11 pages).
International Search Report and Written Opinion for International Patent Application No. PCT/US2011/34516, dated Oct. 20, 2011 (12 pages).
Junker et al., "Wheat amylase trypsin inhibitors drive intestinal inflammation via activation of toll-like receptor 4," J Exp Med. 209(13):2395-408 (2012).
Medlineplus, "Digestive Diseases," <https://www.nlm.nih.gov/medlineplus/ency/article/007447.htm>, retrieved on May 4, 2016 (3 pages).
NCBI Blast Accession No. AY436554. Retrieved Oct. 12, 2011 (1 page).
NCBI Blast Accession No. AY729672. Retrieved Oct. 12, 2011 (1 page).

(Continued)

*Primary Examiner* — Jason Deveau Rosen
(74) *Attorney, Agent, or Firm* — Clark & Elbing LLP

(57) ABSTRACT

The invention features the treatment of gastrointestinal disorders associated with an innate immune response triggered by alpha amylase inhibitor CM3, alpha amylase inhibitor 0.19 (0.19), CM1, CM2, CMa, CMd, CM 16, CMb, CMX1/CMX3, CMX2, and/or alpha amylase inhibitor 0.53 (0.53). To this end, the invention features pharmaceutical compositions including neutralizing antibodies to CM3, 0.19, CM1, CM2, CMa, CMd, CM16, CMb, CMX1/CMX3, CMX2, and/or 0.53, food products containing reduced levels of CM3, 0.19, CM1, CM2, CMa, CMd, CM1 6, CMb, CMX1/CMX3, CMX2, and/or 0.53 protein, the use of oral TLR4 inhibitors to block the effect of said alpha-amylase inhibitors, assays for identifying CM3, 0.19, CM1, CM2, CMa, CMd, CM16, CMb, CMX1/CMX3, CMX2, and/or 0.53 content in food products, and assays for diagnosing subjects with a disorder related to CM3, 0.19, CM1, CM2, CMa, CMd, CM 16, CMb, CMX1/CMX3, CMX2, and/or 0.53 triggered innate immune responses.

5 Claims, 10 Drawing Sheets

Specification includes a Sequence Listing.

(56) References Cited

OTHER PUBLICATIONS

Pastorello et al., "Wheat IgE-mediated food allergy in European patients: alpha-amylase inhibitors, lipid transfer proteins and low-molecular-weight glutenins. Allergenic molecules recognized by double-blind, placebo-controlled food challenge," Int Arch Allergy Immunol. 144(1):10-22 (2007).
Rocher et al., "Identification of the three major coeliac immunoreactive proteins and one alpha-amylase inhibitor from oat endosperm," FEBS Lett. 310(1):37-40 (1992).
Tatham et al., "Allergens in wheat and related cereals," Clin Exp Allergy. 38(11):1712-26 (2008).
Kalunke et al., "Reduction of Allergenic Potential in Bread Wheat RNAi Transgenic Lines Silenced for CM3, CM16, and 0.28 Genes," Int J Mol Sci. 21(16):5817-5834 (2020).
Kerschen et al., "Effectiveness of RNA interference in transgenic plants," FEBS Lett. 566(1-3):223-228 (2004).
Geisslitz et al. "Wheat ATIs: Characteristics and Role in Human Disease," Front Nutr. 8:1-16 (2021).
Barber et al. "New alpha-amylase and trypsin inhibitors among the CM-proteins of barley (*Hordeum vulgare*)," Biochimica et Biophysica Acta. 873:147-151 (1986).
Paz-Ares et al. "The CM-Proteins from Cereal Endosperm: Immunochemical Relationships," J. Exp. Bot. 34:388-395 (1983).
Liwinski et al., "A prospective pilot study of a gluten-free diet for primary sclerosing cholangitis and associated colitis," Aliment Pharmacol Ther. 57(2):224-236, 2022 (13 pages).

Bates et al., "Intestinal Alkaline Phosphatase Detoxifies Lipopolysaccharide and Prevents Inflammation in Response to the Gut Microbiota," Cell Host Microbe. 2(6): 371-382, 2007 (21 pages).
Lallès, "Intestinal Alkaline Phosphastase: Novel Functions and Protective Effects," Nutr Rev. 72(2): 82-94, 2014.
Carroccio et al., "Wheat Consumption Leads to Immune Activation and Symptom Worsening in Patients with Familial Mediterranean Fever: A Pilot Randomized Trial," Nutrients 12(4):1127, 2020 (12 pages).
Sano et al., "Increase in the Lipopolysaccharide Activity and Accumulation of Gram-Negative Bacteria in the Stomach with Low Acidity," Clin Transl Gastroenterol. 11(7):e00190, 2020 (8 pages).
Zevallos et al., "Nutritional Wheat Amylase-Trypsin Inhibitors Promote Intestinal Inflammation via Activation of Myeloid Cells," Gastroenterology. 152(5):1100-1113, 2017 (26 pages).
Caminero et al., "Lactobacilli Degrade Wheat Amylase Trypsin Inhibitors to Reduce Intestinal Dysfunction Induced by Immunogenic Wheat Proteins," *Gastroenterology*. 156(8): 2266-2280, 2019.
Pickert et al., "Wheat consumption aggravates colitis in mice via amylase trypsin inhibitor-mediated dysbiosis," Gastroenterology. 159:257-272, 2020 (33 pages).
Ashfaq-Khan et al., "Dietary wheat amylase trypsin inhibitors promote features of murine non-alcoholic fatty liver disease," Sci Rep. 9(1):17463, 2019 (14 pages).
Guilherme et al., "Dietary Wheat Amylase Trypsin Inhibitors Impact Alzheimer's Disease Pathology in 5xFAD Model Mice," Int J Mol Sci. 21(17):6288, 2020 (17 pages).

* cited by examiner

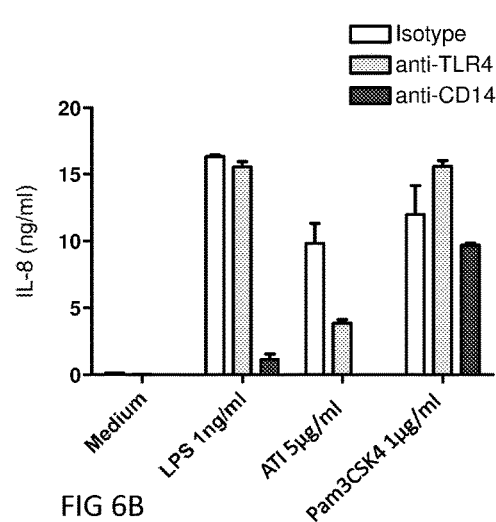
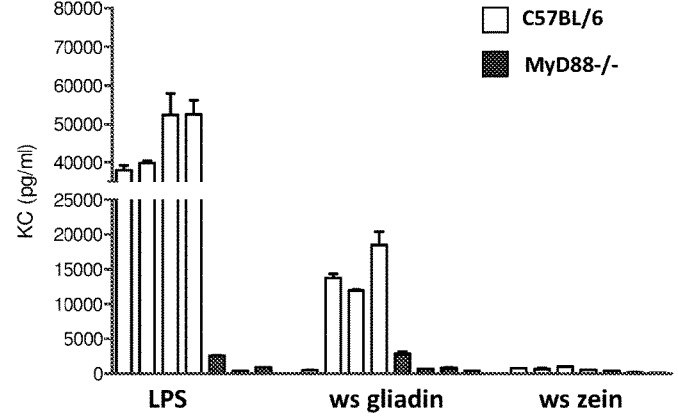
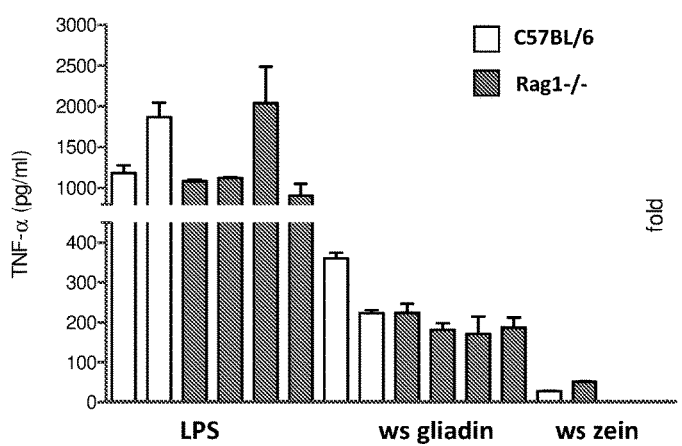
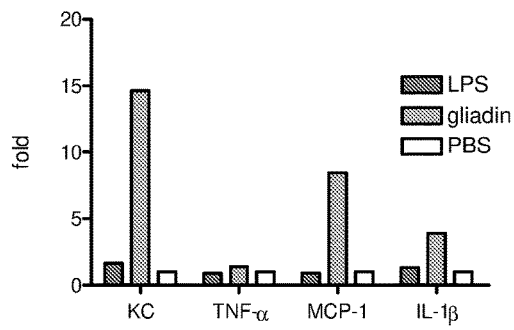
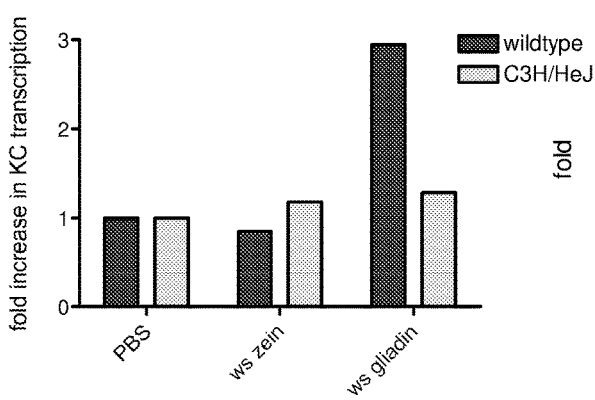
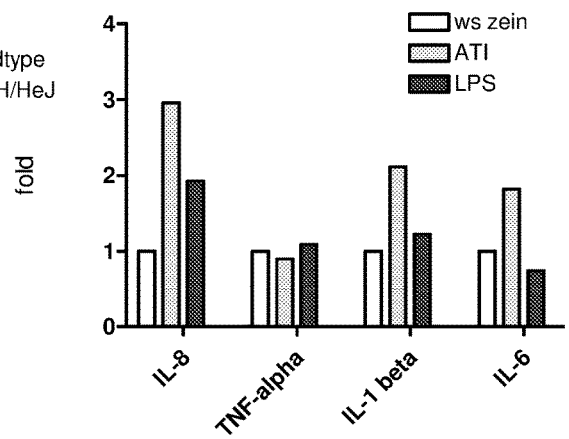

Coomassie   WB: α-FLAG

FIG. 10A

```
CM3   MACKSSCSLLLLAAVLLSVLAAASASGS-QVPGVAFRTNLLPH-CRDYVLQQTCGTFTPGSK  60
0.19  --------------------------SGPWM-CYPQQAFQVPALPA-CRPLLRLQCNGSQVPEAV  37
                                *..  *  **  **;.  ** **    ;   *   *:  .*     :

CM3   LPEWMTSASIYSPGKPYLAKLY-CCQELAEISQC-CNEALRYFIALPVPSQPVDPRSGNVG  120
0.19  LRD-------------------CCQQLAHISEWF-CGALYSMLDSMYKEHGAQE-----G   73
       *  ;                  ***;**.**;  *** **     ;;      .;  .;           *

CM3   ESGLIDLPG-CPREMQWDFVRLLVAPGQCNLATIHN---VRY-CPAVEQPLWI  168
0.19  QAGTGAFPP-CRREVVKLTAASITAVCRLPIVVDASGDGAYV-CKDVAAYPDA  124
       ;;*     ;*  * ***;          ;   ;.*   ;  ; ..     .   *    *
```

FIG. 10B

```
CM1       MASKSSISPLLLATVLVSVFAAATATGPY--CYAGMGLPINPLEG-CREYVAQQT-CGISIS  58
CM2       MASKSSITHLLLAAVLVSVFAAAAATGPY--CYPGMGLPSNPLEG-CREYVAQQT-CGVGIV  58
CMa       MASKSSITPLLLAAVLASVFAAATATGQY--CYAGMGLPSNPLEG-CREYVAQQT-CGVTIA  58
CM3       MACKSSCSLLLLAAVLLSVLAAASASGS---QVPGVAFRTNLLPH-CRDYVLQQT-CGTFTP  57
CMd       MACKSSRSLLLLATVMVSVFAAAAAAATI--SPGVAFPTNLLGHE-CRDYVLQQT-CAVFTP  60
CM16      MASKSN-CVLLLAAVLVSIFAAVAAIGNE--ICTPWMSTLITPLPS-CRDYVEQQA-CRIETP  58
CMb       MASKSS-CDLLLAAVLVSIFAAVAAVGSE--ICTPWTATPITPLPS-CRDYVEQQA-CRIETP  58
CMX1/CMX3 MAFKHQ--LILSTAILLAVLAAASASFRE--QCVPGREITYESLNARREYAVRQT-CGYYLS  57
CMX2      MAFKHQ--LILSTAILLAVLAAASASFRE--QCVPGREITYESLNARREYAVRQT-CGYYLS  57
0.19      ----------------------------SGPW-MCYPGQAFQVPALPA-CRPLLRLQ-CNGSQVP  34
0.53      ----------------------------SGPW-MCYPGQAFQVPALPG-CRPLLKLQ-CNGSQVP  34
                                                *  .        *                *

CM1       GSAVS----------TEPGNTPRDF-CCKELYDASQH-CICEAVRYFIGR--RSDPN-----  101
CM2       GSPVS----------TEPGNTPRDF-CCKELYDASQH-CICEAVRYFIGR--TSDPN-----  101
CMa       GSPVS----------SEPGDTPKDF-CCQELDEAPQH-CICEAVRYFIGR--RSHPD-----  101
CM3       GSKLPEWMTSASIYSPGKPYLAKLY-CCQELAEISQC-CNCEALRYFIALPVPSQPVDPRSG  117
CMd       GSKLPEWMTSAELNYPGQPYLAKLY-CCQELAEIPQQ-CNCEALRYFMALPVPSQPVDPSTG  120
CM16      GS--------------PYLAKQQ-CCGELANIPQQ-CKCQALRYFMGP--KSRPD-----   95
CMb       GP--------------PYLAKQQ-CCGELANIPQQ-CKCQALRFFMGR--KSRPD-----   95
CMX1/CMX3 AE--------------RQKRP-CCDELSKVPEL-KKCEVLRILMDR-----------   87
CMX2      AE--------------RQKRP-CCDELSKVPEL-KKCEVLRILMDR-----------   87
0.19      EA--------------VLRD-CCQQLAHISEWF-CGALYSMLDSMYKEHGAQE----   72
0.53      EA--------------VLRD-CCQQLADISEWF-CGALYSMLDSMYKEHGVSE----   72
                                   **  ;*   .   ;    *     . ;      ;;

CM1       ---SSVLKDLPG-CPREPQRDFAKVLVTSGH-CNVMTVHNAPY-CLGLDI----------  145
CM2       ---SGVLKDLPG-CPREPQRDFAKVLVTPGH-CNVMTVHNTPY-CLGLDI----------  145
CMa       ---WSVLKDLPG-CPKEPQRDFAKVLVTPGQ-CNVLTVHNAPY-CLGLDI----------  145
CM3       NVGESGLIDLPG-CPREMQWDFVRLLVAPGQ-CNLATIHNVRY-CPAVEQPLWI------  168
CMd       NVGQSGLMDLPG-CPREMQRDFVRLLVAPGQ-CNLATIHNVRY-CPAVEQPLWI------  171
CM16      ---QSGLMELPG-CPREVQMDFVRILVTPG-CNLTTVHNTPY-CLAMEESQWS------  143
CMb       ---QSGLMELPG-CPREVQMDFVRILVTPG-CNLTTVHNTPY-CLAMDEWQWNRQFCSS  149
CMX1/CMX3 ------RVTKEGVVKG------SLLQDMSF-CKKLTREFIAGIVGRE----------  121
CMX2      ------RVTKEGVVKD------SLLQDMSF-CKKLTREFIAGIVGRE----------  121
0.19      --GQAGTGAFPP-CRREVVKLTAASITAV-CRLPIVVDASGDGAYV-CKDVAAYPDA---  124
0.53      --GQAGTGAFPS-CRREVVKLTAASITAV-CRLPIVVDASGDGAYV-CKDVAAYPDA---  124
                    ;                ;    ;    .       .
```

METHODS AND COMPOSITIONS FOR TREATING CELIAC DISEASE

CROSS-REFERENCE TO RELATED APPLICATIONS

This application claims benefit of U.S. Provisional Application Nos. 61/330,043, filed Apr. 30, 2010 and 61/417,613 filed Nov. 29, 2010, each of which is hereby incorporated by reference.

STATEMENT AS TO FEDERALLY FUNDED RESEARCH

This work was supported by grant number NIH 1R21AI078385A1-01 from the United States National Institutes of Health. The Government has certain rights in the invention.

SEQUENCE LISTING

The instant application contains a Sequence Listing which has been submitted electronically in ASCII format and is hereby incorporated by reference in its entirety. Said ASCII copy, created on Jul. 31, 2017 is named "Sequence Listing_10302012_ST25.TXT" and is 18,563 bytes in size.

BACKGROUND OF THE INVENTION

This invention relates to the treatment of celiac disease with compounds that decrease inflammation resulting from contact with wheat alpha Amylase inhibitors, including CM3 or 0.19.

Celiac disease (CD) is an inflammatory small intestinal disorder, often accompanied by a malabsorptive syndrome which is caused in part by an uncontrolled immune reaction to ingested gluten proteins. The prevalence of this disease in affected populations such as the US, the Middle East, or Europe is 0.5-2.5%. Untreated, CD patients can develop serious secondary morbidity, such as T cell lymphoma and autoimmune diseases. The disorder is considered to be the result of a complex interplay of intrinsic (genetic) and variable extrinsic (environmental) factors that explain the wide spectrum of clinical manifestations ranging from asymptomatic to severe malabsorption. Gluten peptides are efficiently presented by celiac disease-specific HLA-DQ2- and HLA-DQ8-positive antigen-presenting cells, and thus drive the adaptive immune response, predominantly in the connective tissue of the lamina propria. Tissue transglutaminase (tTG), which has been identified as the highly specific endomysial autoantigen, is increasingly released from cells during inflammation. It usually potentiates antigen presentation by HLA-DQ2 and HLA-DQ8 by deamidating and cross-linking gluten peptides. The result is lamina propria T-cell activation and mucosal transformation by activated intestinal mononuclear cells and fibroblasts.

Currently, celiac disease is typically treated with a strict gluten free diet. However, a gluten free diet is difficult to maintain and non-dietary treatment alternatives are urgently needed. Moreover, even a gluten free diet may not lead to remission in patients with refractory celiac disease.

SUMMARY OF THE INVENTION

The invention features a pharmaceutical composition including an antibody (e.g., a polyclonal, monoclonal, or humanized antibody) against alpha amylase inhibitor CM3, alpha amylase inhibitor 0.19 (0.19), CM1, CM2, CMa, CMd, CM16, CMb, CMX1/CMX3, CMX2, alpha amylase inhibitor 0.53 (0.53), and structurally and functionally related molecules (collectively termed AAI). The antibody can be formulated for, e.g., oral administration (e.g., in milk or colostrum). Furthermore, the antibody can be produced in the milk or colostrum of a mammal (e.g., goat or cow). Also, the antibody can be formulated to be active in the intestine.

In another aspect, the invention features a method of treating a gastrointestinal disorder (e.g., celiac disease, ulcerative colitis, Crohn's disease, or irritable bowel syndrome) by administering any of the pharmaceutical compositions described above or an oral or systemic TLR4 inhibitor (e.g., as described below). The pharmaceutical composition can be administered immediately prior to, during or after a meal, or can be administered, e.g., once, twice, or three times daily.

In another aspect, the invention features a method of determining a substance's potency in inducing a negative gastrointestinal reaction by measuring the AAI content of the substance, where the measurement is indicative of the potency of the substance in inducing a negative gastrointestinal reaction. This method can include dispersing all or a fraction of the substance in an aqueous solution, contacting the solution with an antibody specific for an AAI (e.g., an antibody bound to a substrate) under conditions conducive to specific binding, and measuring the amount of the antibody bound to the AAI. In one embodiment, this method features an ELISA assay.

In another aspect, the invention features a method of testing the sensitivity of a subject to ingestion of AAI containing substances by measuring the levels (e.g., with an ELISA assay) of anti-AAI antibody in sample isolated from the subject (e.g., a blood or stool sample) where the levels are indicative of the sensitivity of the subject to ingestion of AAI containing substances.

In yet another aspect, the invention features a method of reducing the potency of a substance in inducing a negative gastrointestinal reaction by reducing the AAI content of the substance (e.g., through enzymatic degradation, disulfide reduction, or separation of AAI).

In a related aspect, the invention features a cereal product (e.g., wheat, rye, barley, oats, corn or rice) including reduced levels of AAI protein (e.g., through enzymatic degradation, disulfide reduction, separation, or by derivation from cereals engineered to express AAI at decreased levels) compared to levels of AAI in naturally occurring cereal products.

In another aspect, the invention features a nucleic acid construct encoding an RNAi molecule against AAI and a vector including a nucleic acid construct encoding an RNAi molecule against AAI. The invention also features a transgenic plant including any of the above nucleic acid constructs or vectors. These transgenic plants can be processed into food products with decreased AAI content thereby resulting in less potent induction of a negative gastrointestinal reaction in a subject with a gastrointestinal disorder (e.g., celiac disease, ulcerative colitis, and Crohn's disease).

By "wheat alpha Amylase inhibitor AAI", and specifically "CM3" and "0.19," is meant any polypeptide having the activity of full-length CM3 or 0.19 protein:

CM3:
(SEQ ID NO: 1)
MACKSSCSLLLLAAVLLSVLAAASASGSCVPGVAFRTNLLPHCRDYVL
QQTCGTFTPGSLPEWMTSASIYSPGKPYLAKLYCCQELAEISQQCRCE
ALRYFIALPVPSQPVDPRSGNVGESGLIDLPGCPREMQWDFVRLLVAPGQ
CNLATIHNVRYCPAVEQPLWIDYKDDDDK.

-continued
0.19:

(SEQ ID NO: 2)
SGPWMCYPGQADQVPALPACRPLLRLQCNGSQVPEAVLRDCCQQLAHISE
WCRCGALYSMLDSMYKEHGAQEGQAGTGAFPRCRREVVKLTAASITAVCR
LPIVVDASGDGAYVCKDVAAYPD

The terms "wheat alpha Amylase inhibitor CM3", or "CM3", "wheat alpha Amylase inhibitor 0.19," or "0.19" also are used herein to refer to CM3 or 0.19 fragments, which may be, e.g., functional, antigenic, and/or immunogenic. Further, these terms also encompass CM3 or 0.19 polypeptides or fragments including additional terminal amino acids, e.g., an amino terminal methionine.

By "the activity of full-length CM3 protein", or "the activity of full-length 0.19 protein" is meant binding to TLR4 and induction of IL-8 secretion in monocytes, macrophages, or dendridic cells as described herein.

The terms "wheat alpha Amylase inhibitor CM3," "CM3," "wheat alpha Amylase inhibitor 0.19," or "0.19" are also used herein to refer to proteins or peptides having at least 20%, e.g., at least 25%, 30%, 40%, 50%, 60%, 70%, 75%, 80%, or 90% (e.g., 91%, 92%, 93%, 94%, 95%, 96%, 97%, 98%, or 99%) amino acid sequence identity to the sequence of SEQ ID NO:1 or SEQ ID NO:2. Proteins having such amino acid sequence identity can, e.g., have cysteine residues at positions corresponding to the amino acid residue located in the CM3 protein at residue numbers 29, 43, 83, 84, 94, 96, 130, and 159.

The terms "CM1," "CM2," "CMa," "CMd," "CM16," "CMb," "CMX1/CMX3," "CMX2," and "alpha amylase inhibitor 0.53" (0.53) are used herein to refer to protein fragments, which may be, e.g., functional, antigenic, and/or immunogenic. Further, these terms also encompass CM1, CM2, CMa, CMd, CM16, CMb, CMX1/CMX3, CMX2, and 0.53 polypeptides or fragments including additional terminal amino acids, e.g., an amino terminal methionine.

The terms "CM1," "CM2," "CMa," "CMd," "CM16," "CMb," "CMX1/CMX3," "CMX2," and 0.53 are also used herein to refer to proteins or peptides having at least 20%, e.g., at least 25%, 30%, 40%, 50%, 60%, 70%, 75%, 80%, or 90% (e.g., 91%, 92%, 93%, 94%, 95%, 96%, 97%, 98%, or 99%) amino acid sequence identity to the sequence of SEQ ID NOs: 6-11, respectively having the activity of binding to TLR4 and induction of IL-8 secretion in monocytes, macrophages, or dendridic cells as described herein. Proteins having such amino acid sequence identity can, e.g., have cysteine residues at positions corresponding to the amino acid residue located in the CM3 protein at residue numbers 29, 43, 83, 84, 94, 96, 130, and 159.

By "polypeptide," "polypeptide fragment," or "peptide" is meant a chain of two or more (e.g., 10, 15, 20, 30, 50, 100, or 175, or more) amino acids, regardless of any post-translational modification (e.g., glycosylation or phosphorylation), constituting all or part of a naturally or non-naturally occurring polypeptide, fragment, or peptide. By "post-translational modification" is meant any change to a polypeptide or polypeptide fragment made during or after synthesis. Post-translational modifications can be produced naturally (such as during synthesis within a cell) or generated artificially (such as by recombinant or chemical means). A "protein" can be made up of one or more polypeptides.

The term "identity" is used herein to describe the relationship of the sequence of a particular nucleic acid molecule or polypeptide (or a fragment thereof) to the sequence of a reference molecule of the same type (or a fragment thereof). For example, if a nucleic acid or amino acid molecule has the same nucleotide or amino acid residue at a given position, as compared to a reference molecule to which it is aligned, there is said to be "identity" at that position. The level of sequence identity of a nucleic acid molecule or a polypeptide to a reference molecule is typically measured using sequence analysis software with the default parameters specified therein, such as the introduction of gaps to achieve an optimal alignment (e.g., Sequence Analysis Software Package of the Genetics Computer Group, University of Wisconsin Biotechnology Center, 1710 University Avenue, Madison, Wisconsin 53705, BLAST, or PILEUP/PRETTYBOX programs). These software programs match identical or similar sequences by assigning degrees of identity to various substitutions, deletions, or other modifications.

The sequence of a nucleic acid molecule or polypeptide is said to be "substantially identical" to that of a reference molecule if it exhibits, over its entire length, at least 51%, e.g., at least 55%, 60%, 65%, 75%, 85%, 90%, or 95% (e.g., at least 91%, 92%, 93%, 94%, 95%, 96%, 97%, 98%, or 99%) identity to the sequence of the reference molecule. For polypeptides, the length of comparison sequences may be, for example, at least 10, 15, 20, 30, 50, 100, or 175, or more amino acids.

A molecule, e.g., an oligonucleotide probe or primer, a gene or fragment thereof, a cDNA molecule, a polypeptide, or an antibody, can be said to be "detectably-labeled" if it is marked in such a way that its presence can be directly identified in a sample. Methods for detectably labeling molecules are well known in the art and include, without limitation, radioactive labeling (e.g., with an isotope, such as $^{32}P$ or $^{35}S$) and nonradioactive labeling (e.g., with a fluorescent label, such as fluorescein).

By a "substantially pure" polypeptide (e.g., antibody) is meant a polypeptide (or a fragment thereof) that has been separated from proteins and organic molecules that naturally accompany it. Typically, a polypeptide is substantially pure when it is at least 60%, by weight, free from the proteins and naturally occurring organic molecules with which it is naturally associated. For example, the polypeptide can be a polypeptide that is at least 75%, 90%, or 99%, by weight, pure. A substantially pure polypeptide can be obtained, for example, by extraction from a natural source, by expression of a recombinant nucleic acid molecule encoding a polypeptide, or by chemical synthesis. Purity can be measured by any appropriate method, e.g., by column chromatography, polyacrylamide gel electrophoresis, or HPLC analysis.

A polypeptide is substantially free of naturally associated components when it is separated from those proteins and organic molecules that accompany it in its natural state. Thus, a protein that is chemically synthesized or produced in a cellular system that is different from the cell in which it is naturally produced is substantially free from its naturally associated components. Accordingly, substantially pure polypeptides not only include those that are derived from eukaryotic organisms, but also those synthesized in *E. coli*, other prokaryotes, or in other such systems.

An antibody is said to "specifically bind" to a polypeptide or fragment if it recognizes and binds to the polypeptide (e.g., CM3 or 0.19), but does not substantially recognize and bind to other molecules (e.g., non-CM3- or non-0.19-related polypeptides) in a sample, e.g., a biological sample that includes the polypeptide.

By "neutralization" and "neutralizing" is meant partial or complete attenuation of the biological effects of an AAI (e.g., CM3 and/or 0.19) (e.g., a negative gastrointestinal reaction). Such partial or complete attenuation of the biological effects of AAI results from modification, interruption, and/or abrogation of AAI stimulation of the innate immune response (e.g., as exhibited in celiac disease). As one of skill in the art understands, there exist multiple modes of determining whether an agent, for example an antibody is to be classified as neutralizing. Neutralizing antibodies would, for example, block stimulation of monocytes or dendridic cells by AAI (e.g., CM3 and/or 0.19) in the assays described herein (e.g., by decreasing secretion of IL-8 by 70%, 80%, 90%, 95%, 99%, or greater compared to control). Neutralizing antibodies can also block AAI (e.g., CM3 and/or 0.19) binding to TLR4 (e.g., by decreasing binding by 70%, 80%, 90%, 95%, 99%, or greater compared to control).

By "sample" is meant a tissue biopsy, amniotic fluid, cell, blood, serum, urine, stool, or other specimen obtained from a patient or a test subject. For example, ELISA and other immunoassays can be used to measure levels of AAI (e.g., CM3 and 0.19); and PCR or RT/PCR can be used to measure the level of AAI (e.g., CM3 and 0.19) nucleic acid molecules.

By "negative gastrointestinal reaction" is meant an innate immune response triggered by AAI (e.g., CM3 and/or 0.19) that results in undesirable symptoms (e.g., those associated with celiac disease).

By "potency" is meant the degree to which a substance induces an innate immune response against AAI protein (e.g., CM3 and/or 0.19 protein).

By "treating" is meant administering a pharmaceutical composition for prophylactic and/or therapeutic purposes or administering treatment to a subject already suffering from a disease to improve the subject's condition or to a subject who is at risk of developing a disease. As it pertains to gastrointestinal disorders, treating can include improving or ameliorating the symptoms of an undesired immune response triggered by AAI (e.g., CM3 and/or 0.19), and prophylactic treatment can include preventing the progression of a mild gastrointestinal disorder to a more serious form. Treating may also mean to prevent the onset of an negative gastrointestinal reaction.

BRIEF DESCRIPTION OF THE DRAWINGS

FIG. 6A is a graph showing IL-8 secretion in monocyte derived dendritic cells stimulated with ATI and LPS and preincubated with anti-TLR4 or anti-CD14 antibodies. TLR2 agonist Pam3CSK4 served as positive control.

FIGS. 6B and 6C are graphs showing serum cytokine levels in C57BL/6J, MyD88−/− (6B), and Rag1−/− mice (6C) (n=4 animals per group) having undergone intraperitoneal injection of LPS (1 μg/g mouse), ws gliadin (500 μg/g mouse), or ws zein (500 μg/g mouse). Serum was taken 2 hrs after injection and serum cytokine levels were measured by ELISA.

FIGS. 6D, 6E, and 6F are graphs showing cytokine mRNA expression levels in mice gavaged with LPS (20 μg/g mouse weight), ws gliadin (2 mg/g mouse weight), ATI (0.075 mg/g mouse weight), ws zein (2 mg/g mouse weight), or PBS. 4 hrs after gavage the C57BL/6J, C3H/HeJ, and C3H/HouJ mice were euthanized and duodenal samples were snap frozen in liquid nitrogen. Duodenal cytokine mRNA levels were measured by quantitative RT PCR. (n=3 animals per group).

FIGS. 10A and 10B are a sequence alignments. FIG. 10A shows an alignment between CM3 and 0.19. FIG. 10B shows an alignment between CM3 or 0.19 and other ATIs from wheat and barley (CMa, CMb, CMd) (SEQ ID NOs, in order listed are SEQ ID NOs: 3-5, 1, 6-10, 2, and 11). The sequence alignment was prepared using the ClustalW program (2.0.12 version). The highly conserved cysteine residues are boxed. (*), (:), and (.) denote identity, high homology, and low homology, of amino acid residues, respectively. Similarities are much higher among individual ATIs.

DETAILED DESCRIPTION OF THE INVENTION

Figure 1A:
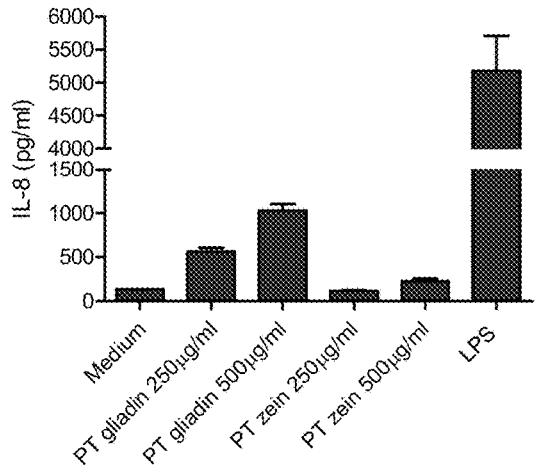
FIGS. 1A-1D are a series of graphs showing IL-8, TNF-α, and MCP-1 release in cells treated with the indicated compounds. The experiments of FIGS. 1A and 1C were conducted in monocytic THP-1 cells and the experiments of FIGS. 1B and 1D were conducted in monocytic U937 cells.
Figure 1B:
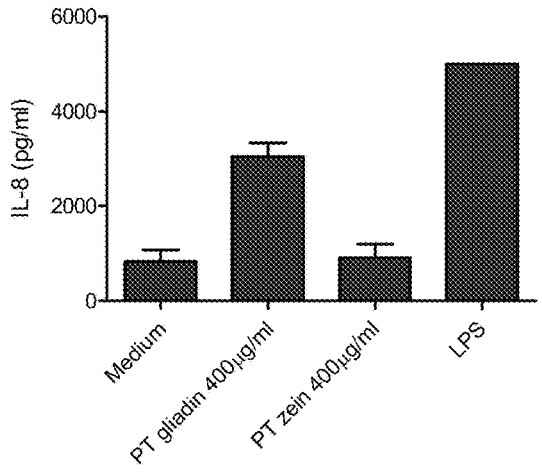
Figure 1C:
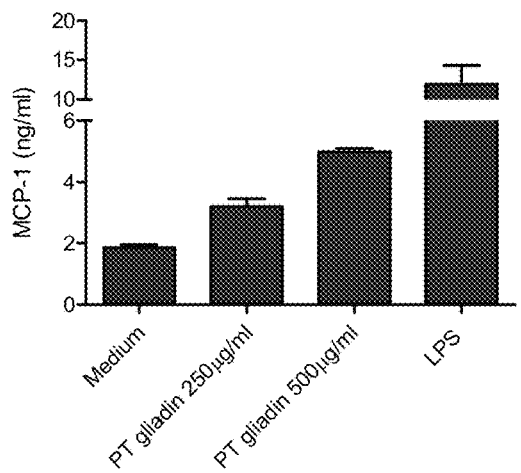
Figure 1D:
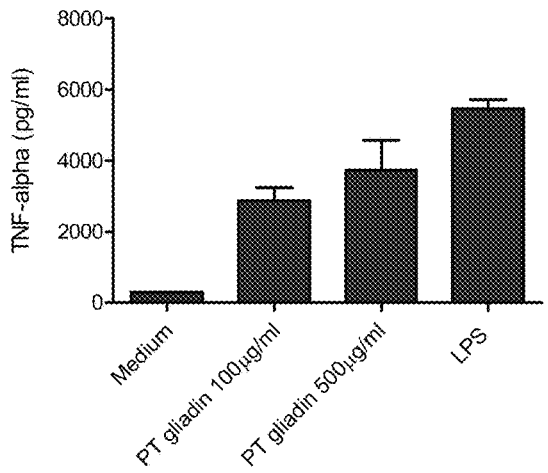
Figure 1E:
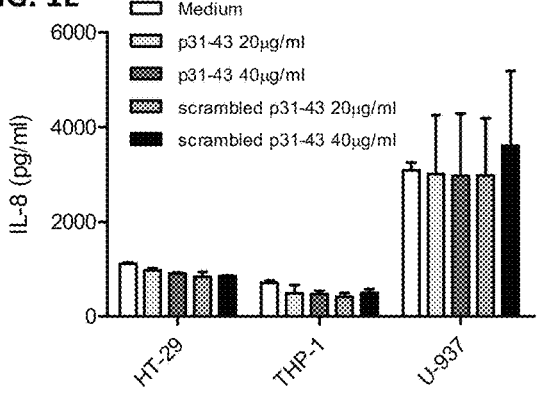
FIG. 1E is a graph showing expression of IL-8 in HT29 (intestinal epithelial), U937, and THP-1 cells treated with alpha-gliadin peptide p31-43 and a scrambled control peptide.
Figure 1F:
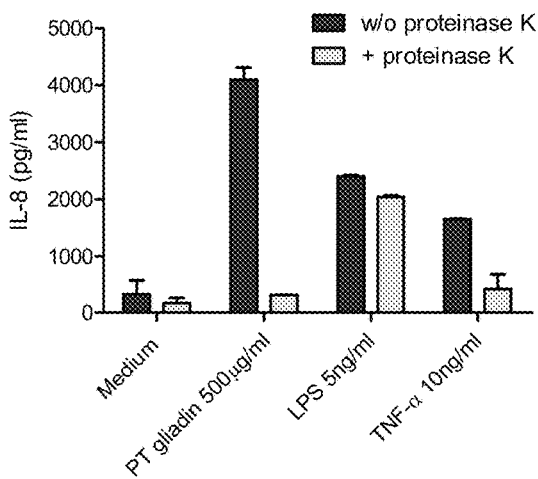
FIG. 1F is a graph showing expression of IL-8 in THP-1 cells treated with the indicated compounds and treated and untreated with proteinase K.
Figure 2A:
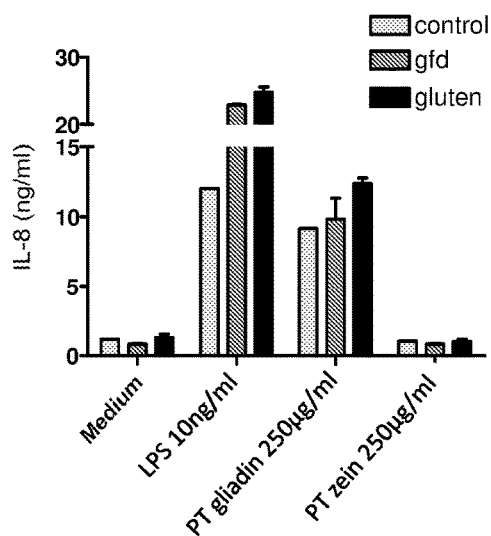
FIG. 2A is a graph showing IL-8 expression in monocyte derived dendritic cells of healthy control patients or of celiac disease patients on the indicated diet treated with the indicated compound.
Figure 2B:
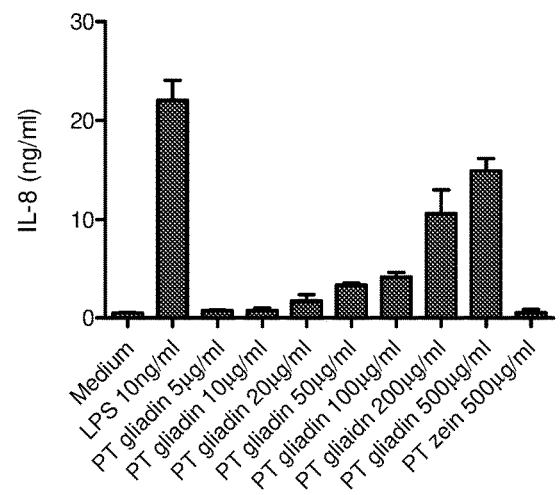
FIG. 2B is a graph showing IL-8 expression of monocyte derived dendritic cells from a healthy control in response to various doses of pepsin/trypsin digested (PT) gliadin. Stimulation with LPS and PT zein served as positive and negative controls, respectively.
Figure 2C:
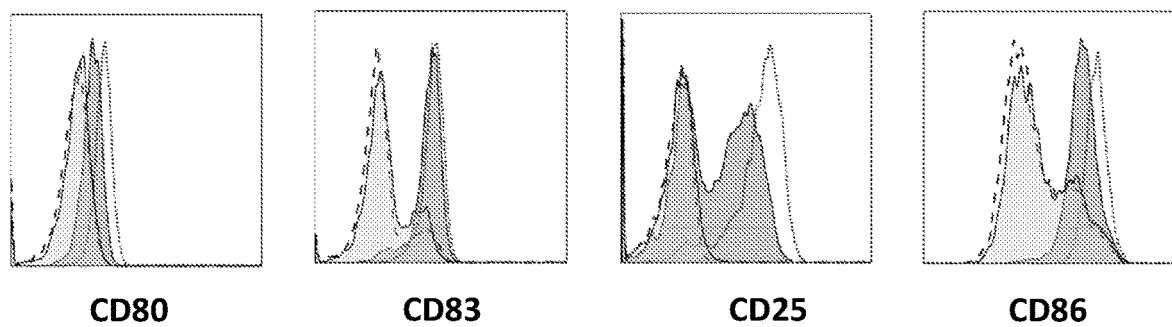
FIG. 2C is a series of graphs showing a flow cytometric analysis of dendritic cells of healthy controls stimulated with PT gliadin. Upregulation of dendritic cell surface maturation markers can be observed in the grey filled and the dotted histogram that represent PT gliadin and LPS stimulation, respectively, whereas PT zein stimulation (non filled) overlaps with the non stimulated control.
Figure 3A:
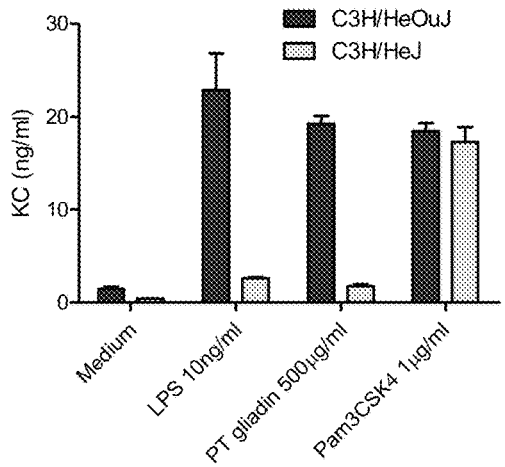
FIGS. 3A and 3B are graphs showing KC (rodent IL-8) and INF-α expression in peritoneal macrophages isolated from TLR4 deficient C3H/HeJ mice compared to C3H/HOuJ wildtype mice stimulated with LPS or PT gliadin. The TLR2 agonist Pam3CSK4 served as positive control.
Figure 3B:
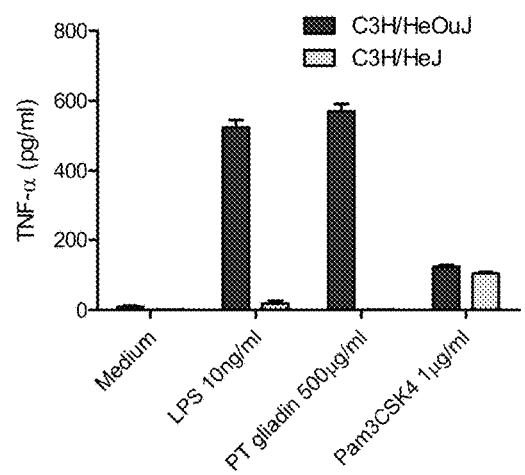
Figure 3C:
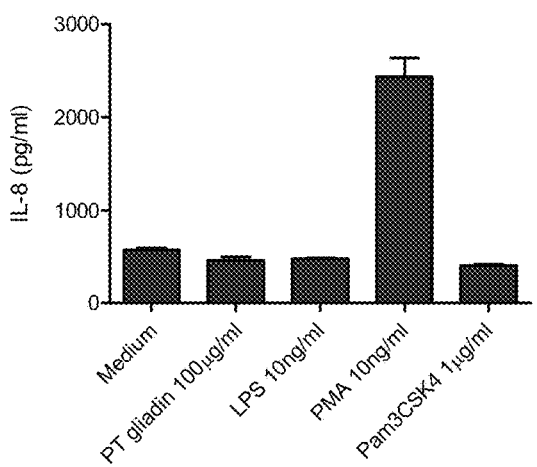
FIGS. 3C and 3D are graphs showing expression of IL-8 secretion upon PT gliadin and LPS stimulation in 293 cells transfected with the TLR4-MD2-CD14 complex (3D) and in non transfected cells (3C). LPS and PMA served as positive, the TLR2 agonist Pam3CSK4 as negative controls.
Figure 3D:
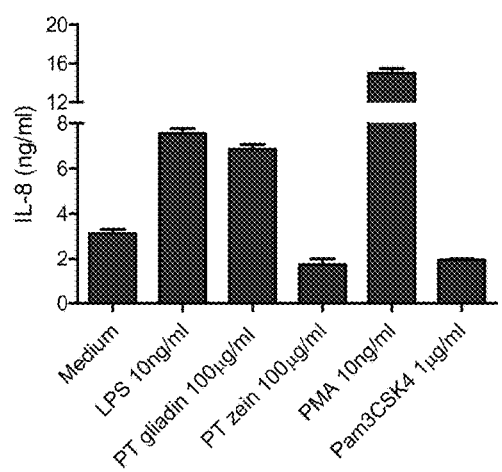
Figure 3E:
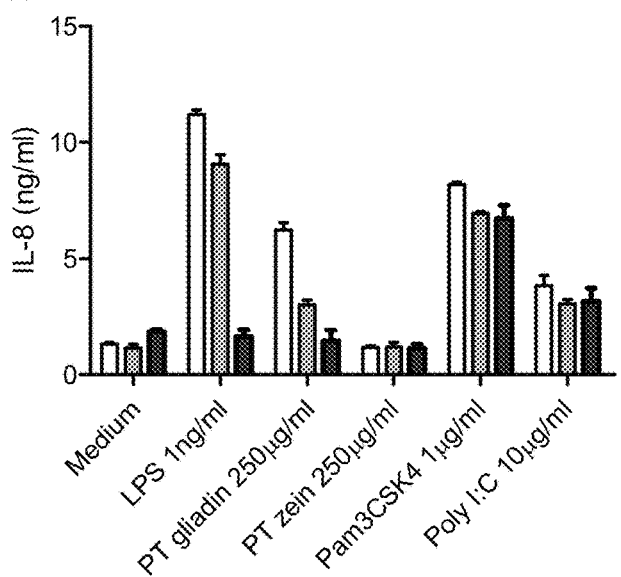
FIG. 3E is a graph showing IL-8 secretion in monocyte derived dendridic cells stimulated with PT gliadin and LPS with peritoneal macrophages preincubated with anti-TLR4 and anti-CD14 antibodies. TLR2 agonist Pam3CSK4 and TLR3 agonist Poly I:C served as positive controls.

In general, the invention features the treatment of gastrointestinal disorders associated with an innate immune response triggered by alpha amylase inhibitor CM3, alpha amylase inhibitor 0.19 (0.19), CM1, CM2, CMa, CMd, CM16, CMb, CMX1/CMX3, CMX2, alpha Amylase Inhibitor 0.53 (0.53) (collectively termed AAI), and other structurally and functionally related molecules. To this end, the invention provides pharmaceutical compositions including neutralizing antibodies to alpha amylase inhibitor CM3, alpha amylase inhibitor 0.19 (0.19), CM1, CM2, CMa, CMd, CM16, CMb, CMX1/CMX3, CMX2, alpha Amylase Inhibitor 0.53 (0.53), and other structurally and functionally related molecules, food products containing reduced levels of AAI proteins, assays for identifying AAI protein content in food products, and assays for diagnosing subjects with a disorder related to AAI-triggered innate immune responses. The invention also features methods of treating gastrointestinal disorders associated with an innate immune response to these molecules with preferably, but not exclusively orally active TLR4 inhibitors.

CM3

We discovered that CM3 and/or 0.19 (among other AAIs) contributes to the activation of innate immunity in patients with celiac disease. An exemplary wheat CM3 protein has the sequence of

```
                                            (SEQ ID NO: 1)
MACKSSCSLLLLAAVLLSVLAAASASGSCVPGVAFRTNLLPHCRDYVL
QQTCGTFTPGSLPEWMTSASIYSPGKPYLAKLYCCQELAEISQQCRCEA
LRYFIALPVPSQPVDPRSGNVGESGLIDLPGCPREMQWDFVRLLVAPGQ
CNLATIHNVRYCPAVEQPLWIDYKDDDDK.
```

An exemplary wheat 0.19 protein has the sequence of:

```
                                            (SEQ ID NO: 2)
SGPWMCYPGQAFQVPALPACRPLLRLQCNGSQVPEAVLRDCCQQLAHISE
WCRCGALYSMLDSMYKEHGAQEGQAGTGAFPRCRREVVKLTAASITAVCR
LPIVVDASGDGAYVCKDVAAYPD
```

The invention provides methods for the treatment of negative gastrointestinal reactions to other cereal-based (e.g., barley, rye, oats, corn, and rice) CM3 or 0.19 proteins, or related molecules, e.g., those set forth in Tables 1 and 2.

TABLE 1

| Accession | Description |
| --- | --- |
| P17314.1 | Alpha-amylase/trypsin inhibitor CM3; |
| P11643.2 | Alpha-amylase/trypsin inhibitor CMd; [*Hordeum vulgare*] |
| CAA49536.1 | CMd subunit of tetrameric alpha-amylase inhibitor [*Hordeum vulgare*] |
| AAB63440.1 | CMd3 protein [*Hordeum vulgare*] |
| CAA31585.1 | CMd preprotein (AA -14 to 146) [*Hordeum vulgare* subsp. *vulgare*] |
| 1208404B | trypsin/amylase inhibitor pUP38 |
| P16159.1 | Alpha-amylase/trypsin inhibitor CM16; [*Triticum aestivum*] |
| P32936.2 | Alpha-amylase/trypsin inhibitor CMb; [*Hordeum vulgare* subsp. *vulgare*] |

TABLE 2

| Accession | Description |
| --- | --- |
| HSSA | Alpha-amylase/trypsin inhibitor 0.19 [*Triticum aestivum*] |
| HSSB | Alpha-amylase/trypsin inhibitor 0.19 [*Triticum aestivum*] |
| HSSC | Alpha-amylase/trypsin inhibitor 0.19 [*Triticum aestivum*] |
| HSSD | Alpha-amylase/trypsin inhibitor 0.19 [*Triticum aestivum*] |
| PO1085.1 | Alpha-amylase/trypsin inhibitor 0.19 [*Aegilops tauschii*] |
| BAA20139.1 | Alpha-amylase/trypsin inhibitor 0.19 [*Aegilops tauschii*] |

A sequence comparison with a wide spectrum of other ATIs from wheat and barley (those sequences that are published in common sequence databases) show again largely conserved cysteine residues and neighbouring amino acid residues (FIG. 10B), indicating that these will also bind to and activate TLR4. Additional variants of CM3 and 0.19 and related molecules are known in the art and can be identified through standard means.

TLR4 Inhibitors

TLR4 inhibitors for pharmaceutical use are known in the art. Such inhibitors include synthetic gluco-disaccharides such as RSCL-0409 (Kalluri et al. FEBS J. 2010 April; 277(7):1639-52); TLR4 (MD2-TLR4) blocking antibodies (Ungaro et al. Am J Physiol Gastrointest Liver Physiol. 2009 June; 296(6):G1167-79); phosphatidyl-ethanolamine (Lee et al. Mol Cells. 2009 Feb. 28; 27(2):251-5); peptide antagonists (Slivka et al. Chembiochem. 2009 Mar. 2; 10(4):645-9); eritoram tetrasodium, E5564 (Rossignol et al. Innate Immun. 2008 December; 14(6):383-94; Kim et al. Cell. 2007 Sep. 7; 130(5):906-17; and Shimamoto et al. Circulation. 2006 Jul. 4; 114(1 Suppl):I270-4); tetra- or penta-acetylated lipid A (Zhang et al. Org Biomol Chem. 2008 Sep. 21; 6(18):3371-81; Coats et al. J Immunol. 2005 Oct. 1; 175(7):4490-8); blocking LPS variants such as LPS from cyanobacteria, *Rhodobacter capsulates*, *Porphyromonas gingivalis* and *Capnocytophagatochracea* or *Helicobacter pylori* (Ianaro et al. Mini Rev Med Chem. 2009 March; 9(3):306-17; Jemmett et al. Infect Immun. 2008 July; 76(7):3156-63; and Macagno A, et al. J Exp Med. 2006 Jun. 12; 203(6):1481-92), Bartonella Quintana (Popa et al. Infect Immun. 2007 October; 75(10):4831-7), *Treponema* (Lee et al. Microbiology. 2006 February; 152(Pt 2):535-46), or lipid IVa (Saitoh et al. Int Immunol. 2004 July; 16(7):961-9); E5531 (Bryant et al. Vet Immunol Immunopathol. 2007 Apr. 15; 116(3-4):182-9); soluble MD-2/TLR4 complex (Mitsuzawa et al. J Immunol. 2006 Dec. 1; 177(11):8133-9); including indirect negative modulators of TLR4 (MD2-TLR4), such as vitamin D (Sadeghi et al. Eur J Immunol. 2006 February; 36(2):361-70), testosterone derivatives (Norata et al. J Clin Endocrinol Metab. 2006 February; 91(2): 546-54), CRX526 (Ianaro et al.), or inhibitors of the nicotinic acetylcholine receptor (Hamano et al. Shock. 2006 October; 26(4):358-64). Each of the above references is incorporated by reference in its entirety.

Any of the agents employed according to the present invention may be contained in any appropriate amount in any suitable carrier substance, and is generally present in an amount of 1-95% by weight of the total weight of the composition. The composition may be provided in a dosage form that is suitable for the oral, parenteral (e.g., intravenously, intramuscularly), rectal, cutaneous, nasal, vaginal, inhalant, skin (patch), or ocular administration route. Thus, the composition may be in the form of, e.g., tablets, capsules, pills, powders, granulates, suspensions, emulsions, solutions, gels including hydrogels, pastes, ointments, creams, plasters, drenches, osmotic delivery devices, suppositories, enemas, injectables, implants, sprays, or aerosols. The pharmaceutical compositions may be formulated according to conventional pharmaceutical practice (see, e.g., Remington: The Science and Practice of Pharmacy, 20th edition, 2000, ed. A. R. Gennaro, Lippincott Williams & Wilkins, Philadelphia, and Encyclopedia of Pharmaceutical Technology, eds. J. Swarbrick and J. C. Boylan, 1988-1999, Marcel Dekker, New York).

Indications

The invention provides methods for the treatment of AAI (e.g., CM3- and/or 0.19)-related gastrointestinal disorders by administering a subject (e.g., a human) in need thereof an effective amount of a composition that includes an antibody against an AAI protein (e.g., CM3), or a different antibodies against the major AAI variants in cereals. Such disorders are related to the induction of an innate immune response against AAI proteins (e.g., against CM3 and/or 0.19) after the consumption of an AAI containing food product. These disorders include celiac disease, ulcerative colitis, Crohn's disease, irritable bowel syndrome, gastrointestinal hypersensitivity to wheat, as well as other inflammatory disease of the GI tract and related immune and autoimmune disorders.

Anti-AAI Antibodies

The invention provides therapeutic antibodies (e.g., neutralizing antibodies) and diagnostic antibodies against AAI, e.g., against CM3 and/or 0.19.

The antibodies (e.g., monoclonal, polyclonal, poly-specific, or mono-specific antibodies) against AAI (e.g., against CM3 and/or 0.19) can be used for diagnostic, research, or therapeutic purposes. Numerous methods for making antibodies are known in the art and can be used in the invention to make such antibodies. In one example, a coding sequence for an AAI (e.g., a CM3 and/or 0.19) peptide or polypeptide is expressed as a C-terminal fusion with glutathione S-transferase (GST) (Smith et al., Gene 67:31, 1988). The fusion protein is purified on glutathione-Sepharose beads, eluted with glutathione, cleaved with thrombin (at an engineered cleavage site), and purified for immunization of rabbits. Primary immunizations are carried out with Freund's complete adjuvant and subsequent immunizations with Freund's incomplete adjuvant. Antibody titers are monitored by Western blot and immunoprecipitation analyses using the thrombin-cleaved protein fragment of the GST fusion protein. Immune sera are affinity purified using CNBr-Sepharose-coupled protein. Antiserum specificity can be determined using a panel of unrelated GST proteins.

As an alternate or adjunct immunogen to GST fusion proteins, peptides corresponding to relatively unique immunogenic regions of a polypeptide of the invention can be generated and coupled to keyhole limpet hemocyanin (KLH) through an introduced C-terminal lysine. Antiserum to each of these peptides is similarly affinity purified on peptides conjugated to BSA, and specificity is tested by ELISA or Western blot analysis using peptide conjugates, or by Western blot or immunoprecipitation using the polypeptide expressed as a GST fusion protein. Alternatively, monoclonal antibodies that specifically bind an AAI (e.g., CM3 or 0.19) can be prepared using standard hybridoma technology (see, e.g., Kohler et al., Nature 256:495, 1975; Kohler et al., Eur. J. Immunol. 6:511, 1976; Kohler et al., Eur. J. Immunol. 6:292, 1976; Hammerling et al., Monoclonal Antibodies and T Cell Hybridomas, Elsevier, N Y, 1981). Once produced, monoclonal antibodies can also be tested for specific recognition by Western blot or immunoprecipitation analysis. Antibodies that specifically recognize an AAI protein (e.g., CM3 or 0.19) can be used, for example, in immunoassays or as therapies. Alternatively monoclonal antibodies can be prepared using the polypeptide of the invention described above and a phage display library (Vaughan et al., Nature Biotech. 14:309, 1996).

Antibodies of the invention can be produced using fragments of the AAI (e.g., a CM3 and/or 0.19) polypeptide that lie outside generally conserved regions and appear likely to be antigenic by criteria such as high frequency of charged residues. In one specific example, such fragments are generated by standard techniques of PCR and cloned into the pGEX expression vector. Fusion proteins are expressed in *E. coli* and purified using a glutathione agarose affinity matrix.

To minimize potential problems of low affinity or specificity of antisera, two or three such fusions are generated for each protein, and each fusion is injected into at least two rabbits. Antisera are raised by injections in a series, and can include, for example, at least three booster injections.

In addition to intact monoclonal and polyclonal anti-AAI (e.g., anti-CM3 and/or 0.19) antibodies, the invention also includes various genetically engineered antibodies, humanized antibodies, chimeric antibodies, and antibody fragments, including F(ab')2, Fab', Fab, Fv, and sFv fragments. Truncated versions of monoclonal antibodies, for example, can be produced by recombinant methods in which plasmids are generated that express the desired monoclonal antibody fragment(s) in a suitable host. Antibodies can be humanized by methods known in the art, e.g., monoclonal antibodies with a desired binding specificity can be commercially humanized (Scotgene, Scotland; Oxford Molecular, Palo Alto, CA). Fully human antibodies, such as those expressed in transgenic animals, are also included in the invention (Green et al., Nature Genetics 7:13-21, 1994).

Examples of approaches that can be used to generate antibodies of the invention include the following. Ladner (U.S. Pat. Nos. 4,946,778 and 4,704,692) describes methods for preparing single polypeptide chain antibodies. Ward et al., Nature 341:544-546, 1989, describes the preparation of heavy chain variable domains, which they term "single domain antibodies," and which have high antigen-binding affinities. McCafferty et al., Nature 348:552-554, 1990, shows that complete antibody V domains can be displayed on the surface of fd bacteriophage, that the phage bind specifically to antigen, and that rare phage (one in a million) can be isolated after affinity chromatography. Boss et al., U.S. Pat. No. 4,816,397, describes various methods for producing immunoglobulins, and immunologically functional fragments thereof, that include at least the variable domains of the heavy and light chains in a single host cell. Cabilly et al., U.S. Pat. No. 4,816,567, describes methods for preparing chimeric antibodies.

Antibodies to AAI (e.g., to CM3 or 0.19) can be used, as noted above, to detect AAI, or to inhibit the biological activities of AAI. In addition, the antibodies can be coupled to compounds, such as radionuclides and liposomes, for diagnostic uses.

In order to generate polyclonal antibodies on a large scale and at a low cost an appropriate animal species can be chosen. Polyclonal antibodies can be isolated from the milk or colostrum of, e.g., immunized cows. Bovine colostrum contains 28 g of IgG per liter, while bovine milk contains 1.5 g of IgG per liter (Ontsouka et al. J. Dairy Sci. 86:2005-2011, 2003). Polyclonal antibodies can also be isolated from the yolk of eggs from immunized chickens (Sarker et al. J. Ped. Gastro. Nutr. 32:19-25, 2001).

Multiple adjuvants are approved for use in dairy cows. Adjuvants useful in this invention include, but are not limited to, Emulsigen®, an oil-in-water emulsified adjuvant, Emulsigen®-D, an oil-in-water emulsified adjuvant with DDA immunostimulant, Emulsigen®-P, an oil-in-water emulsified adjuvant with co-polymer immunostimulant, Emulsigen®-BCL, an oil-in-water emulsified adjuvant with block co-polymer immunostimulant, Carbigen™, a carbomer base, and Polygen™, a co-polymer base. All of the listed adjuvants are commercially available from MVP Laboratories in Omaha, NE.

Antibodies useful in this invention can be identified in several different screening assays. First, antibodies are assayed by ELISA to determine whether they are specific for the immunizing antigen (e.g., CM3 and/or 0.19). Using standard techniques, ELISA plates are coated with immunogen, the antibody is added to the plate, washed, and the presence of bound antibody detected by using a second antibody specific for the Ig of the species in which the antibody was generated.

A functional in vitro assay can be used to screen antibodies e.g., an neutralizing assay based on monocyte derived dendritic cells, as described herein.

Direct measurements of bovine immunoglobulin in illeal fluid in human subjects has shown that significant amounts of immunoglobulin survive transit through the stomach and small intestine (Warny et al. Gut, 44:212-217, 1999). Methods have also been described to formulate avian immunoglobulin (IgY) for GI delivery (Kovacs-Nolan and Mine Immunol. Methods. 296: 199-209, 2005).

The invention provides a therapeutic composition comprising anti-AAI (e.g., anti-CM3 and/or anti-0.19) antibodies suitable for delivery, preferably oral delivery, to a patient in need thereof, preferably a human patient. The pharmaceutical composition may further comprise suitable carriers, adjuvants and other physiologically acceptable excipients.

The invention also features a therapeutic composition containing antibodies with specificity for both the CM3 of SEQ ID NO:1 (or proteins substantially identical to the protein of SEQ ID NO:1) and/or the 0.19 of SEQ ID NO:2 (or proteins substantially identical to the protein of SEQ ID NO:2) as well as additional CM3- or 0.19-related proteins (e.g., CM3 or 0.19 analogs expressed in other species of cereals or other AAI proteins as disclosed herein). Such antibodies can be identified by testing specificity to all of the desired CM3- or 0.19-related proteins.

Furthermore, the invention also features pharmaceutical compositions containing a plurality of antibodies, where different antibodies in the composition are specific for different analogs of AAI (e.g., CM3 and/or 0.19). Additionally or alternatively, such compositions can contain antibodies against both AAI CM3 and/or 0.19), as well as gluten (e.g., gliadin and glutenin fractions, see, e.g., WO 2007/056301, which is herein incorporated by reference in its entirety). Such pharmaceutical compositions can be achieved by mixing more than one source of antibodies, or, e.g., inoculating an antibody producing animal with more than one AAI (e.g., a cow can be inoculated with variants of CM3 and/or 0.19 with adjuvants as described above thereby creating a mixture of polyclonal antibodies with differing specificities).

The oral formulations can comprise enteric coatings, so that the active agent is delivered to the intestinal tract. Enteric formulations are often used to protect an active ingredient from the strongly acid contents of the stomach. Such formulations are created by coating a solid dosage form with a film of a polymer that is insoluble in acid environments and soluble in basic environments. Exemplary films are cellulose acetate phthalate, polyvinyl acetate phthalate, hydroxypropyl methylcellulose phthalate, and hydroxypropyl methylcellulose acetate succinate, methacrylate copolymers and cellulose acetate phthalate.

The pharmaceutical compositions can be administered in any orally acceptable dosage form including, but not limited to, capsules, tablets, aqueous suspensions or solutions.

Neutralizing antibodies can be administered to a patient prior to, or concurrently, or after the ingestion of a substance that may contain an AAI (e.g., CM3 and/or 0.19). The neutralizing antibodies of the invention can also be administered to the patient on a regular dosing schedule (e.g., one, two, three times a day, or more). The neutralizing antibodies can also be administered at a specific time of day, e.g., prior to sleep or upon wakening.

Detection and measurement of indicators of efficacy may be measured by a number of available diagnostic tools, including but not limited to, for example, by physical examination including blood tests, biopsies of the small intestine, pulmonary function tests, and chest X-rays; CT scan; bronchoscopy; bronchoalveolar lavage; lung biopsy and CT scan. Suppression of the innate immunity can be measured, e.g., by quantifying the release of cytokines at the sites of lesions. Also, both the physician and patient can identify a reduction in symptoms of a disease.

The pharmaceutical compositions of this invention comprise any of the compounds of the present invention, or pharmaceutically acceptable derivatives thereof, together with any pharmaceutically acceptable carrier.

The dosage and dose rate of the compounds of this invention effective to produce the desired effects will depend on a variety of factors, such as the nature of the antibody, the size of the subject, the goal of the treatment, the nature of the pathology to be treated, the specific pharmaceutical composition used, and the judgment of the treating physician. Dosage levels of between about 0.1 and about 1000 mg/kg body weight per dose, preferably between about 1 and about 500 mg/kg body weight per dose of the active ingredient antibody are useful. The antibodies of the invention can also be administered at a dose ranging between about 1 mg/kg body weight/dose and about 200 mg/kg body weight/dose, and between about 5 mg/kg body weight/dose and about 50 mg/kg body weight/dose.

Detection Assays

The invention features assays for detecting AAI (e.g., CM3 and/or 0.19) in food products. The assays can contain, e.g., antibodies as described above. Such antibodies can be antibodies specific for AAI proteins (e.g., CM3 and/or 0.19), and can have neutralizing or non-neutralizing activities. Such antibodies can be detectably labeled to facilitate detection. Assays for detecting proteins in a sample (e.g., a food product) are known in the art (e.g., ELISA or RIA assays). Such assays can be readily adapted to detection of AAI (e.g., CM3 and/or 0.19).

The invention also features assays for detecting antibodies against AAI (e.g., CM3 or 0.19) in a patient sample (e.g., using an ELISA assay as described above). Such assays can be used, e.g., to diagnose a patient as being sensitive to AAI (e.g., sensitive to CM3 and/or 0.19, and as having celiac disease, ulcerative colitis, Crohn's disease, or irritable bowel syndrome). The patient sample can be any sample likely to contain antibodies against AAI (e.g., a blood sample or stool sample). The presence or heightened levels of endogenously generated antibodies against AAI can be indicative of a subject as being sensitive to AAI containing food products.

AAI Depleted Food Products

The invention also features food products with decreased levels of AAI (e.g., CM3 and/or 0.19). Such food products can be prepared, e.g., by degrading or removing AAI prior to consumption. Such food products can also be prepared from transgenic cereals (e.g., wheat) containing nucleic acid constructs encoding RNAi molecules against AAI.

Decreased levels of AAI (e.g., CM3 and/or 0.19) protein can be achieved, e.g., through disulfide reduction of AAI. This can be achieved by agents such dithioerithrol, or preferably by a NADP-thioredoxin system as described by Farid et al. (J Agricult Food Chem 56:7146-7150, 2008) for the improvement of digestability of soy flour. The latter and related methodologies have the advantage that disulfide reduction is non-toxic. The reduced AAIs are then easily degraded by gastric and duodenal proteases, leading to their "detoxification," i.e., inability to elicit an innate immune response. To secure complete degradation before ingestion, the reduced AAIs can be predigested with common proteases such as pepsin, trypsin, or chymotrypsin, or with specialized enzyme preparations.

Decreased levels of AAI (e.g., CM3 and/or 0.19) can also be achieved by separating AAI from the food product by, e.g., exposing the food product to antibodies specific for AAI. Such antibodies can be used, e.g., in a purification column to remove AAI from a solution containing AAI.

Methods for silencing gene expression in plants is well understood in the art. The current invention features RNAi molecules specific for an AAI (e.g., against a nucleic acid sequence corresponding to the amino acid sequence of SEQ ID NO:1 and/or SEQ ID NO:2). Such RNAi molecules can be expressed from a nucleic acid construct introduced into a plant cell. Desirably, expression of the RNAi construct would result in a decrease of CM3 and/or 0.19 expression in the food product of 50%, 60%, 70%, 80%, 90%, 95%, 99%, or greater.

In a specific embodiment, virus induced gene silencing (VIGS) can be used to decrease CM3 (or other AAIs) expression in, e.g., wheat or other cereals. In this embodiment, a plant virus (e.g., barley stripe mosaic virus) is engineered to contain a sequence with substantial identity to a the genomic nucleic acid sequence corresponding to CM3 (or other AAIs). This technology is reviewed, e.g., in Cakir et al. (Crop Sci. 50:S-1-S-8, 2010), which is hereby incorporated by reference in its entirety.

Experimental Results

Figure 8A:
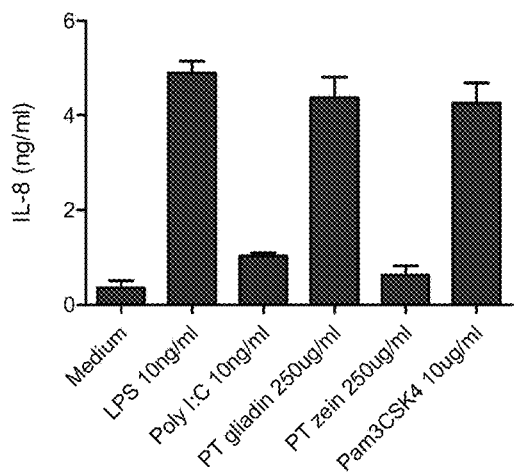
FIGS. 8A-8C are supplementary graphs showing expression of IL-8 (8A), TNF-α (8B), and RANTES (8C) in gliadin stimulated human monocyte derived DC from healthy controls.
Figure 8B:
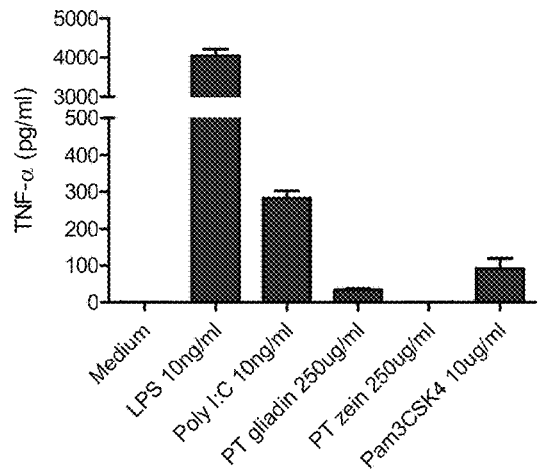
Figure 8C:
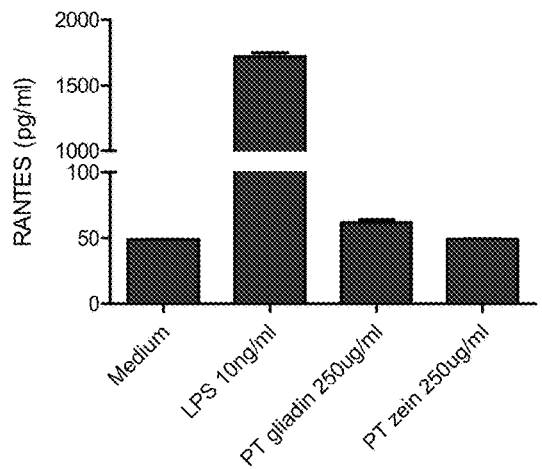

To examine how far gliadin elicits innate immune responses, we stimulated the human monocytic cell lines THP-1 and U937 with different concentrations of gliadin digested with pepsin and trypsin (PT gliadin) and measured secretion of proinflammatory cytokines in the supernatant. A digest of zein, partly homolgous storage proteins from corn that lack toxicity for patients with celiac disease, served as negative control. In accordance with other studies, only PT gliadin but not PT zcin caused a dose dependent stimulation of IL-8, TNF-α, and MCP-1 secretion in both cell lines (FIG. 1). To rule out LPS contamination as trigger of innate responses, gliadin, LPS, and TNF-α were digested with proteinase K, completely digesting and abrogating all peptide-related activities. As expected, TNF-α lost its stimulatory capacity, while LPS was still able to induce IL-8. Importantly, PT gliadin was equally inactivated (FIG. 1), indicating that the stimulatory effects of gliadin were due to protein and not LPS contamination. Moreover, while IL-8 expression was comparable, human monocyte-derived dendritic cells (DC) stimulated with PT gliadin expressed TNF-α and RANTES to a much lesser extent than the LPS stimulated control (FIG. 8).

It was shown previously that the α-gliadin peptide p31-43 increases IL-15 secretion in celiac biopsies. However, this peptide did not elicit secretion of IL-8, TNF-α, or MCP-1 in our monocytic or intestinal epithelial cell lines (HT29, Caco-2 and T84), even at 40 μg/ml (FIG. 1). This suggested the presence of other potent peptide stimulators of innate immune responses in PT gliadin.

We then analyzed human DC derived from peripheral blood monocytes of celiac patients on gluten free diet (gfd, n=8), on regular diet (n=3) and healthy controls (n=10). Although there were considerable inter-individual variations, all cells strongly reacted to gliadin stimulation by IL-8 secretion. Of note, there were no significant differences in sensitivity towards PT gliadin between celiac patients on or off gluten free diet and healthy controls, confirming recent data that demonstrated comparable activation of PT gliadin-stimulated DC from controls and CD patients. Again, PT zein had no effect on cytokine production (FIGS. 2A-2D).

When exposed to PT gliadin and LPS, DC also up-regulated the cell surface maturation markers CD25, CD80, CD83, and CD86 while zein showed no effect (FIG. 2E).

A recent study suggested that gliadin may signal via MyD88, a key adapter molecule in the toll-like receptor (TLR)/IL-10 pathway. Since MyD88 transmits signals from several TLRs, we studied peritoneal macrophages of C3H/HeJ mice that lack TLR4 responses due to a spontaneous point mutation in the TLR4 gene. In these mice KC (IL-8) and TNF-α secretion was reduced to baseline levels after gliadin or LPS stimulation compared to syngenic C3H/HeOuJ TLR4 competent mice. In macrophages from both mouse strains the specific TLR2 agonist Pam3CSK4 induced equally high amounts of KC and TNF-α, verifying otherwise intact MyD88 and TLR signaling and viability of the cells (FIGS. 3A-3D).

To confirm a key role of TLR4 in the innate immune response to gliadin extract, we used HEK-293 cells (that do not express TLR4 or TLR2) that were transfected with the human TLR4-CD14-MD2-complex. While non-transfected HEK-293 cells responded neither to gliadin nor to LPS stimulation, both stimulants induced an increase of IL-8 secretion in the transfected cells. Specificity of the transfection was demonstrated by the absence of IL-8 induction by the TLR2 agonist Pam3CSK4 (FIG. 3).

In order to examine whether gliadin also engages TLR4 in human dendritic cells, we preincubated monocyte derived DC with anti-TLR4 and CD14 blocking antibodies before adding the stimulants. This significantly reduced IL-8 production in DC stimulated with gliadin and LPS but not with the TLR2 and TLR3 agonists Pam3CSK4 and Poly-I:C, respectively, both in DC from healthy controls (FIG. 3E) and from celiac disease patients.

Figure 4A:
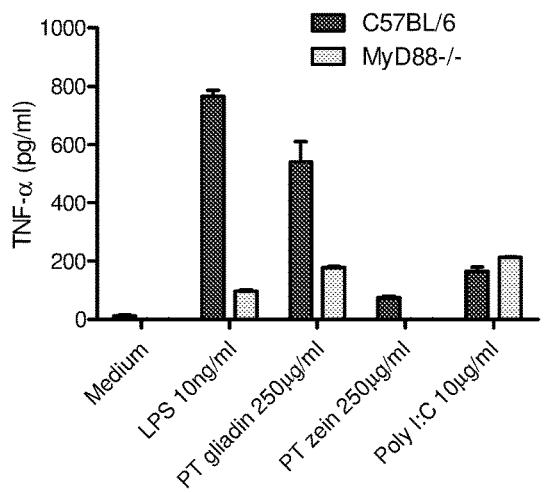
FIG. 4A is a graph showing TNF-alpha secretion in peritoneal macrophages isolated from MyD88−/− mice compared to C57BL/6 wildtype mice upon PT gliadin stimulation. LPS served as positive control for the MyD88 knockdown, TLR3 agonist Poly I:C served as cell viability control.

TLR4 is unique in its ability to mediate cellular activation via two pathways: the adapter molecule MyD88 or via interferon regulatory factor 3 (IRF3) pathway. Compared to C57BL/6J wildtype mice, peritoneal macrophages from MyD88 knockout mice displayed markedly reduced KC and TNF-α secretion after gliadin and LPS stimulation, indicating a major involvement of the MyD88 pathway. Since TLR3 does not use MyD88 as adapter protein for signaling, we used the TLR3 agonist Poly PC as positive control (FIG. 4A).

Figure 4B:
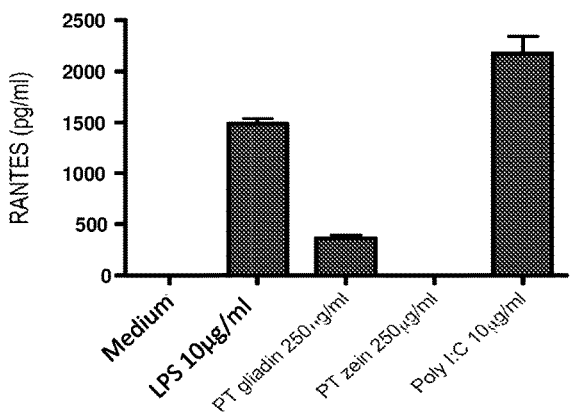
FIG. 4B is a graph showing RANTES secretion in peritoneal macrophages isolated from C57BL/6J mice upon LPS, Poly I:C and PT gliadin stimulation.

To analyze potential activation of the alternate pathway, we measured the secretion of RANTES in supernatants of macrophages from C57BL/6J wildtype mice. RANTES secretion was increased, suggesting that both the MyD88 dependant and independent pathway are activated by the gliadin extract (FIG. 4B). Taken together, we can conclude that gliadin-induced signaling is mediated via TLR4, MyD88, and TRIF, and is CD14 dependent.

Figure 4C:
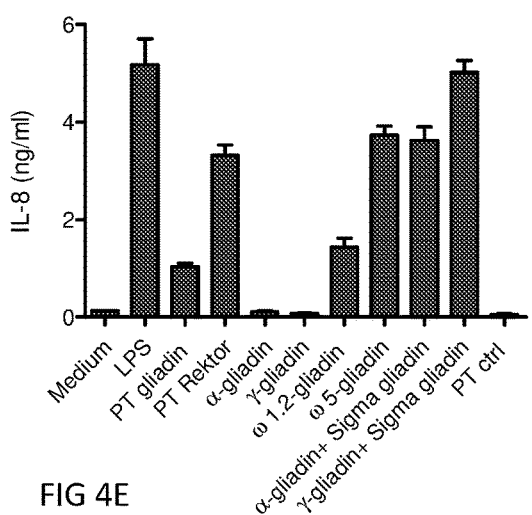
FIG. 4C is a graph showing stimulation of THP-1 cells with α-, γ-, ω1.2 and ω5-gliadin fractions isolated from the pure wheat strain 'Rektor'. Co-incubation of α- and γ-gliadin with regular PT gliadin from Sigma served as cell viability control.
Figure 4D:
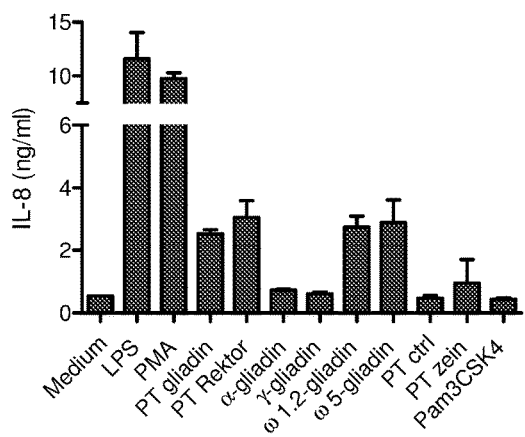
FIGS. 4D and 4E are graphs showing IL-8 secretion in TLR4 transfected (4D) and untransfected (4E) HEK-293 cells treated with co-gliadins.
Figure 4E:
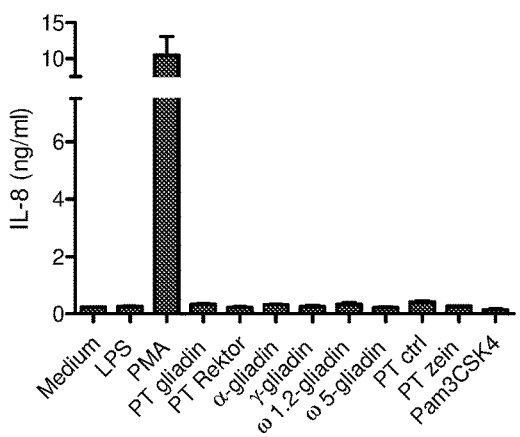

We then proceeded to further define the gliadin fractions that harbored the stimulatory activity. Gliadins from the pure wheat strain "Rektor" were separated into their α-, γ- and ω-fractions via HPLC. The α-, γ-, ω1-2-, and ω5-gliadins, as well as whole gliadin were digested with pepsin and trypsin and first tested on THP-1 monocytic cells. Neither the α- nor the γ-gliadins which represent more than 90% of total gliadin harbored stimulatory activity, whereas IL-8 release was induced strongly by PT-digested ω1-2- and ω5-gliadins (FIG. 4C). The lack of stimulation by α- or γ-gliadin was not due to toxic by-products, since addition of LPS or whole PT gliadin fully restored stimulatory capacity (FIG. 4C). As shown for whole PT gliadin, ω1-2- and ω5-gliadin strongly induced IL-8 secretion in TLR4 transfected HEK-293 but not in untransfected HEK-293 cells (FIGS. 4D and 4E).

Figure 4F:
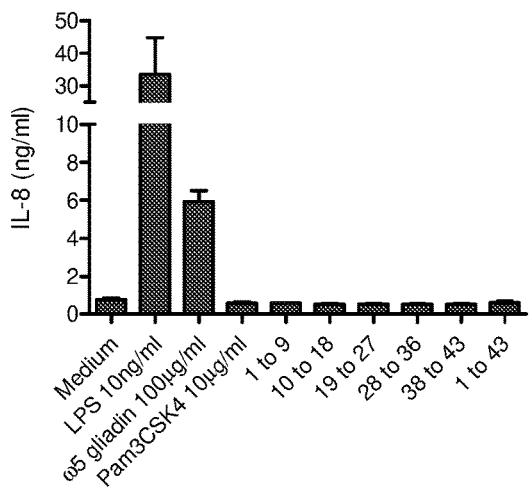
FIG. 4F is a graph showing IL-8 secretion in TLR4 transfected HEK-293 cells treated with synthetic overlapping 20mers of ω5-gliadin. For illustration purposes, nine fractions each were pooled in the stimulation experiments, as well as all 43 fractions. LPS served as positive and Pam3CSK4 or PT zein as negative controls.

Next, we used synthetic overlapping 20mers of the ω5 gliadin chain to identify the TLR4-stimulating peptide sequence using TLR4-CD14-MD2-transfected FMK cells and IL-8 secretion for a readout. Surprisingly, none of the synthetic peptides triggered IL-8 secretion (FIG. 4F). This negative finding could have been due to posttranslational modifications of the gliadin or due to a particular secondary structure that might not have been captured by the synthetic peptides. However, since most gliadins are not significantly modified posttranslationally and since their secondary structure is well reflected even by smaller peptides, we searched for other wheat proteins that might have co-purified with the ω gliadins. In comassie staining, one minor protein band with a molecular mass of 15 kD clearly distinguished the ω- from the non-reactive α- and γ-gliadin fractions. When analyzed by mass spectrometry, it could be tentatively characterized as wheat alpha amylase inhibitor CM3 and/or 0.19. As part of the albumin fraction, wheat alpha amylase inhibitors (AAIs) are highly disulfide-linked and water soluble proteins. It has been shown that they partly co-purify with gliadin and glutenin preparations. Notably, the fraction of the omega-gliadins appears to contain much of the low molecular weight albumins that contain AAIs. Thus a water-soluble gliadin fraction showed the same properties as the PT (omega) gliadins but with an even higher stimulatory capacity than PT gliadin (FIG. 5E) and SDS-PAGE demonstrated a more prominent band with a molecular weight of 15 kD which again was confirmed as AAI by mass spectrometry.

Figure 5A:
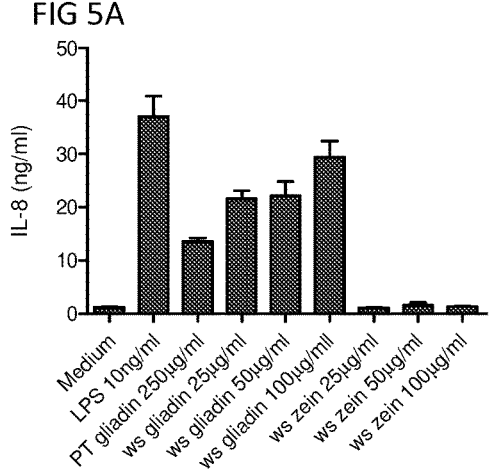
FIGS. 5A and 5B are graphs showing KC expression by monocyte derived dendritic cells stimulated with water-soluble (ws) gliadin (5A) or alpha amylase trypsin inhibitor (ATI, 5B).
Figure 5B:
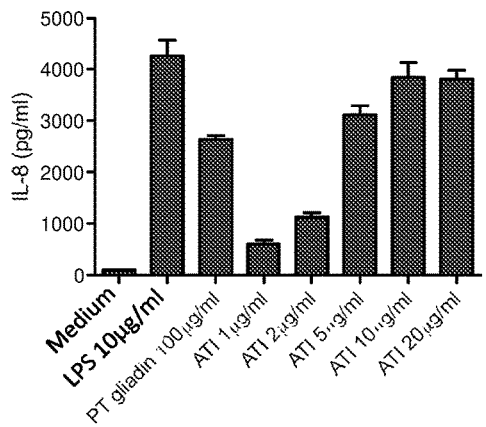
Figure 5C:
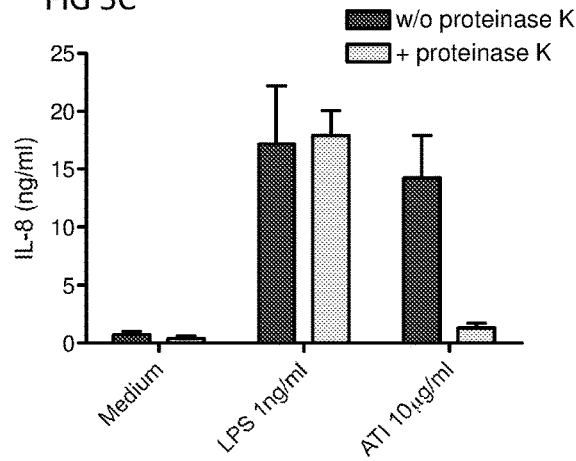
FIG. 5C is a graph showing IL-8 secretion in dendritic cells treated with a proteinase K digestion of ATI and LPS.
Figure 5D:
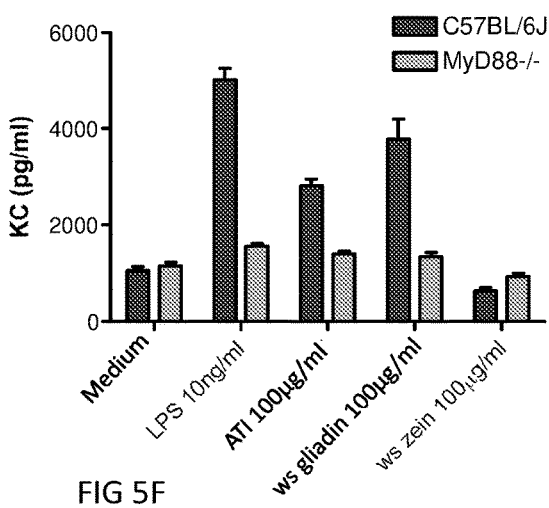
FIG. 5D is a graph showing KC secretion in peritoneal macrophages isolated from MyD88−/− mice compared to C57BL/6J wildtype mice upon ATI or ws gliadin stimulation.
Figure 5E:
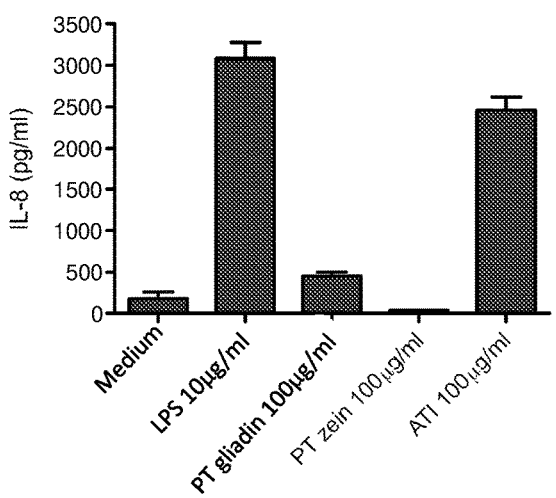
FIGS. 5E and 5F are graphs showing IL-8 secretion upon PT gliadin, ATI, or LPS stimulation in 293 cells transfected with the TLR4-MD2-CD14 complex (5E) and in non transfected cells (5F). LPS and water-soluble zein served as positive and negative controls, respectively.
Figure 5F:
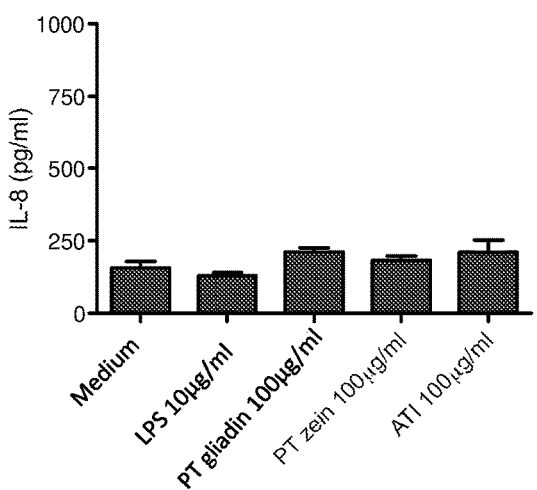
Figure 7A:
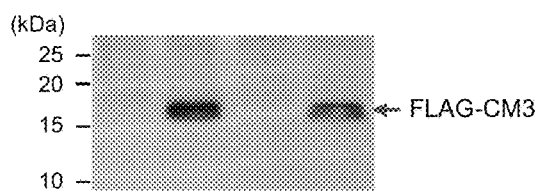
FIG. 7A is a western blot showing the major ATI variant CM3 was expressed in eukaryotic 293 cells and purified as Flag-tagged molecule, yielding the expected molecular weights of 16 kD.
Figure 7C:
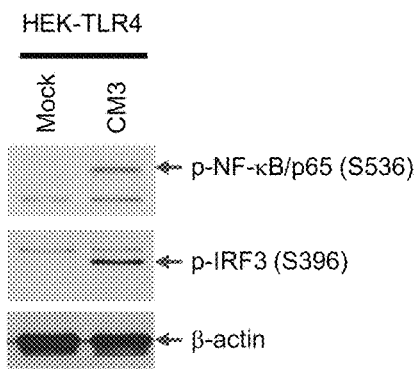
FIG. 7C is a western blot showing expression of NF-kB and the alternative (IRF3) pathways in CM3 and TLR4-transfected HEK cells.
Figure 7B:
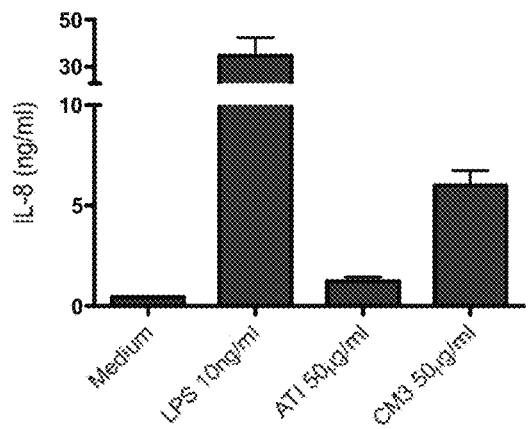
FIG. 7B is a graph showing IL-8 secretion in human dendritic cells upon stimulation with ATI and the recombinant CM3 variant.
Figure 7D:
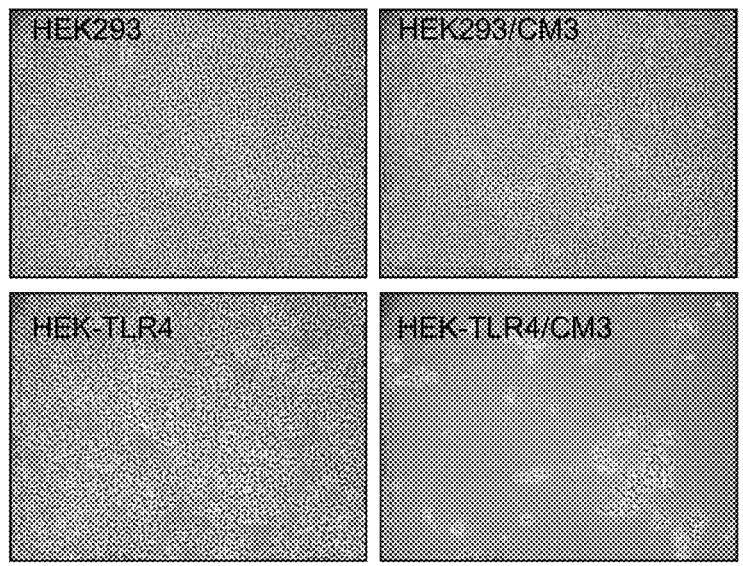
FIG. 7D is a photomicrograph showing apoptosis in TLR4- and CM3-transfected and untransfected HEK cells.

Subsequently, we used AAI purified from wheat seed to stimulate human monocyte derived dendritic cells. HPLC analysis of this preparation showed one major peak confirming its purity. Both untreated and PT-digested AAI induced increased IL-8 secretion (FIG. 5), while proteinase K digestion abrogated its stimulatory capacity, ruling out LPS contamination (FIGS. 5D and 5E). AAI was then incubated with peritoneal macrophages from MyD88−/− and C57BL/6J wildtype mice, showing a lack of KC secretion in MyD88−/− compared to wild type cells. Moreover, AAI induced upregulation of IL-8 secretion in TLR4/MD2/CD14 transfected HEK-293 as compared to untransfected cells (FIGS. 5D-5F), and incubation of human monocyte derived DC with blocking TLR4 and CD14 antibodies prior to addition of ATI reduced IL-8 secretion (FIG. 6C). Overall, these results confirmed the signaling pathways previously identified with crude or co-gliadin and demonstrated that it was indeed AAI that mediated the innate immune responses.

To examine whether the in vitro responses translated into physiologically relevant in vivo responses, we used water-soluble gliadin (which was available in larger quantities) in most experiments and AAI for select studies. When injected intraperitoneally, water-soluble gliadin lead to an increase in peripheral KC and TNF-α levels comparable to LPS, whereas water-soluble zein did not induce a response. No responses were found in MyD88−/− mice, neither with LPS nor with water-soluble gliadin (FIG. 6A). A recent study implicated the adaptive immune system in modulating the innate immune response. We therefore injected water-soluble gliadin into T and B cell deficient Rag1−/− mice. Rag1−/− mice showed cytokine levels similar to the ones elicited in C57BL/6J mice, indicating that the innate response was largely independent of adaptive immunity (FIG. 6B).

Next we analyzed local intestinal effects of orally ingested ATI. To this end C57BL/6J mice were gavaged with LPS, water-soluble gliadin, or PBS, followed by measurement of transcript levels of inflammatory cytokines in the proximal duodenum. Only with water-soluble gliadin did we detect a significant upregulation of duodenal KG, MCP-1, and IL-1β (but not TNF-α) transcripts (FIG. 6D). Of note, LPS did not increase any of these cytokines, which is likely due to its inactivation by low pH in the stomach or by intestinal alkaline phosphatase during intestinal passage. When the same experiment was performed in TLR4 deficient C3H/HeJ mice and the corresponding wild type mice, an increase in duodenal KC transcripts was only observed in the wild type mice. Since water-soluble zein did not induce cytokine transcripts, an unspecific reaction to uncommon nutritional antigens could be ruled out (FIG. 6E).

Experiments were also performed with purified alpha amylase inhibitor, in order to confirm this protein antigen as trigger of wheat-induced innate immune response. When we gavaged C57BL/6 mice with LPS, AAI, and water-soluble zein, AAI was indeed able to increase transcript levels of KC, IL-1β, and IL-6 but not TNF-α in the duodenal mucosa (FIG. 6F). While initially the observed effects appeared less significant when purified AAI was used instead of water-soluble gliadin, this can be explained by the much lower AAI concentrations used in these experiments (0.075 mg of purified protein vs. 2 mg of gliadin extract per g mouse weight).

AAI CM3 and 0.19 were recombinantly expressed in eukaryotic HEK 293 cells, in order to exclude bacterial contaminants, to ensure correct folding, and to identify which of both molecules was the active compound. The affinity purified proteins were used to stimulate monocyte derived DCs. Here, CM3, and to a lesser degree 0.19, upregulated IL-8 secretion, suggesting that CM3 as well as 0.19 AAI were the active compound (FIG. 7).

Figure 9A:
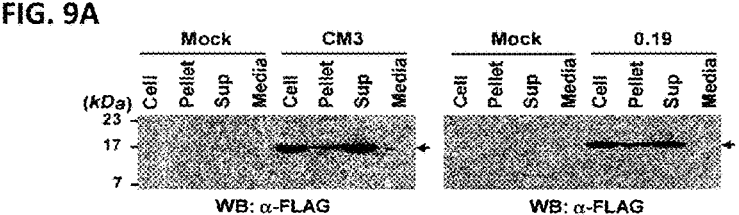
FIG. 9A is a western blot showing CM3 and 0.19 expression in HEK-293 cells and purification as Flag-tagged molecules. Western analysis yielded the expected molecular weights of 15 and 17 kDa, respectively, after 15% SDS-PAGE and Western blotting with Flag antibody. No expression in mock (vector only) transfected cells. 0.19 was not secreted into media, but could be recovered in SDS/DTT buffer (Cell), deoxycholate and Triton X-100 buffer (Sup), or the remaining cell pellet.
Figure 9B:
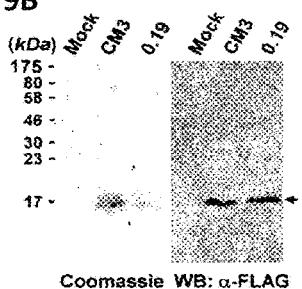
FIG. 9B is a Coomassie blue stain (left panel) or western blot using Flag antibody (right panel) showing purity of CM3 and 0.19 ATI after affinity purification on Flag-agarose (15% SDS-PAGE).
Figure 9C:
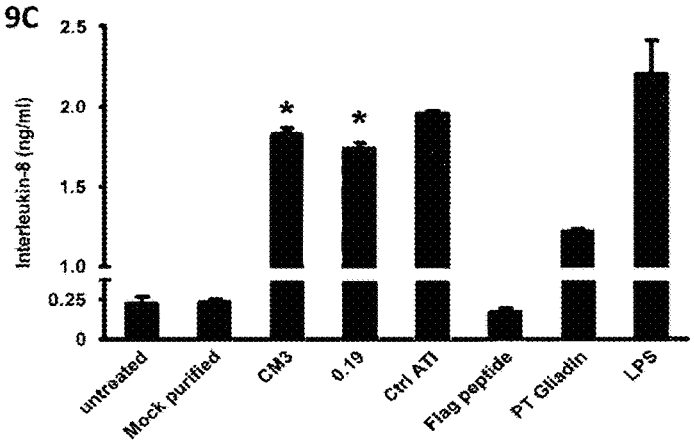
FIG. 9C is a graph showing IL-8 secretion by TLR4-CD14-MD2 expressing HEK-293 cells treated with recombinant ATI. Cells were left untreated, or stimulated with affinity purified detergent extracts from mock-transfected cells, from recombinant CM3, 0.19, or with ATI isolated from wheat (all 5 μg/ml). Controls were Flag peptide (5 μg/ml), PT-gliadin (100 μg/ml), and LPS (10 ng/ml). Representative experiment performed in triplicate.
Figure 9D:
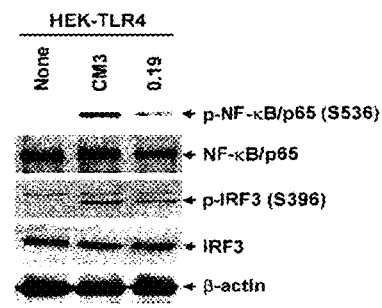
FIG. 9D is a western blot showing expression of CM3 and 0.19 in TLR4-CD14-MD2 expressing HEK-293 cells (HEK-TLR4) induces downstream signaling of the canonical (p-NF-κB/p65) and the alternative (p-IRF3) pathways. Western blots of whole cell lysates (50 μg protein).

CM3 and 0.19, the main ATI family members, were detected by mass spectrometry and were recombinantly expressed in eukaryotic HEK-293 cells to prevent bacterial contaminants (LPS) and to ensure correct protein folding (FIGS. 9A and B). Both affinity purified ATIs stimulated TLR4/MD2/CD14-transfected but not untransfected HEK-293 cells confirming their TLR4-stimulating activity. In line with eukaryotic expression, the stimulatory activity of recombinant CM3 and 0.19 was maintained after additional purification using an endotoxin depletion column (FIG. 9C). In addition, overexpression of both CM3 and 0.19 in TLR4/MD2/CD14 expressing HEK-293 cells strongly induced the canonical and the alternative TLR4-pathway (FIG. 9D). Sequence comparison revealed that despite significant differences in primary sequence, both CM3 and 0.19 showed 5 stretches of highly conserved amino acid residues clustered around cysteins, indicative of a similar secondary structure of both ATIs (FIG. 10A), Other ATI variants (i.e., AAIs) that occur in wheat or barley showed similar homology, suggestive of comparable biological activity (FIG. 10B).

Materials

Purified cell culture tested LPS (*E coli* 055:B5) and in wheat alpha-amylase inhibitor (AAI) type I were purchased from Sigma-Aldrich (St Louis, MO), the TLR2 agonist N-Palmitoyl-S-[2,3-bis(palmitoyloxy)-(2RS)-propyl]-[R]-cysteinyl-[S]-seryl-[S]-lysyl-[S]-lysyl-[S]-lysyl-[S]-lysine x3 HCl (Pam3CSK4) and the TLR3 agonist Polyinosine-polycytidylic acid (poly-I:C)) were obtained from Invivogen (San Diego, CA). Other reagents were of the highest purity available and, if not mentioned otherwise, obtained from Sigma-Aldrich.

Isolation of Gliadin Fractions and PT-Gliadin

Unless otherwise stated gliadin purchased from Sigma-Aldrich (G3375) was used for experiments. Gliadin from the pure wheat strain 'Rektor' was subfractionated as described in the art. Briefly, α, γ, ω1.2 and ω5 gliadins were obtained by HPLC purification on a Nucleosil C8 column (4.6×240 mm) at 50° C., using 0.1% trifluoroacetic acid as phase A, and 99.9% acetonitrile plus 0.1% trifluoroacetic acid as phase B, and a gradient from 24% B to 56% B in 30 min. Detection was at 210 nm. Purity of the fractions was confirmed by SDS PAGE, aminoterminal sequence analysis and their characteristic amino acid composition.

Pepsin-trypsin-digested (PT-) gliadin was generated as originally described with minor modifications. Briefly, gliadin was digested with pepsin in 0.1M HCL (pH 1.8) at 37° C. for 4 hrs, followed by pH adjustment to 7.8 and digestion with trypsin at 37° C. for 4 hrs (substrate:enzyme ratio of 1:200 for both reactions). Adjustment of the pH to 4.5 resulted in a precipitate which was removed by centrifugation at 2,500 rpm, and N-tosyl-chloromethyl-ketone was added to inhibit residual trypsin activity. The supernatant containing the PT-gliadin was dialyzed against 10 mM ammonium carbonate, pH 7.8 (molecular weight exclusion 1000D, Spectra/Por®, Serva, Heidelberg, Germany), sterile-filtered and lyophilized. A parallel digest of zein from corn (Sigma-Aldrich) was used as negative control.

The water soluble fraction of gliadin was obtained by incubating 10 g of gliadin in 50 ml sterile water at 37° C. for 8 hrs under continuous stirring. Insolubles were removed by centrifugation and the supernatant was sterile filtered and lyophilized.

Synthetic Peptides

Peptide p31-43 of α-gliadin (sequence LGQQQPFPPQQPY (SEQ ID NO:3) and a scrambled control peptide (sequence GLQPFQQPQPPQY (SEQ ID NO:4)) were synthesized by AnaSpec Inc. (San Jose, CA). Purity of the peptides was >80% according to HPLC and mass spectrometry analysis. Forty-three 20mer peptides with an overlap of ten amino acids covering the 440 residue omega 5 gliadin were synthesized at 60-80% purity by Primm Biotechnology (Cambridge, MA).

Cell Culture and In Vitro Stimulation Experiments

THP-1, U937, HEK-293 (all from ATCC, Manassas, VA), and HEK-293 cells stably transfected with the TLR4-CD14-MD2 complex (Invivogen) were cultured in complete RPM or DMEM (Cellgro, Manassas, VA) supplemented with penicillin/streptomycin and 10% fetal calf serum at 37° C. in a 5% $CO_2$ atmosphere.

For isolation of peripheral monocytes 40 ml blood was obtained from 11 patients with celiac disease during their diagnostic workup (median 37 years, range 18-59 years), after prior informed consent Eight patients were on gluten free diet and in clinical remission, three patients were newly diagnosed and therefore on a regular gluten containing diet Control monocytes were from the buffy coat of leukopheresis concentrates of anonymous blood donors. Whole EDTA blood or leukapheresis concentrates were subjected to density gradient centrifugation over Ficoll-Hypaque (GE Healthcare, Pittsburgh, PA) and CD14-positive monocytes purified by MACS separation according to the manufacturer's protocol (Miltenyi, Bergisch Gladbach, Germany). For generation of dendritic cells, monocytes were cultured in RPMI supplemented with 10% fetal calf serum, 200 U/ml rhIL-4 and 300 U/ml rhGM-CSF (both from PeproTech, Rocky Hill, NJ) for 6-8 days.

Murine resident peritoneal macrophages were isolated by peritoneal lavage using a 3 ml syringe and 18 G needles.

Three 3 ml of sterile PBS was injected into the peritoneal cavity and reaspirated after gentle massage of the abdomen. For further purification MACS separation for CD11b positive cells was done according to the manufacturer's protocol (Miltenyi).

For stimulation cells were seeded on polystyrene wells at a density of 1×10⁶/ml. Unless otherwise stated supernatants were harvested after a 16 hr incubation with various stimulants.

Exclusion of LPS Contamination

To prove that stimulatory effects were due to protein, PT-gliadin, the wheat ATI, LPS, or TNFα were incubated with or without 20 µg/ml proteinase K (Promega, Madison, WI) for 4 hrs at 56° C. After proteinase K inactivation by boiling for 5 minute the digests were used for cell stimulation.

Animals

C3H/HeJ, C3H/HeOuJ and Rag1−/− mice were obtained from The Jackson Laboratory (Bar Harbour, ME). The MyD88−/− mice were a kind gift from S. Akira, (Osaka University, Osaka, Japan). Congenic C57BL/6J mice served as experimental controls and were bred under the same conditions in the same facility. All experiments were done with mice at age 5-7 weeks.

In Vivo Experiments

Mice were injected intraperitoneally with water-soluble gliadin, zein (500 µg/g body weight) or LPS (1 µg/g) in 200 µl PBS, or PBS alone (negative control). 2 hrs after injection, mice were euthanized by ketamine/xylazine administration and blood was drawn by intraorbital bleeding.

For gavage experiments mice were either raised on gluten free diet (C57BL/6J and MyD88−/− mice) or put on gluten free diet for at least two weeks (C3H/HeJ, C3H/HeOuJ mice), and starved the night before the experiment. Gluten free feed was obtained from Research Diets (New Brunswick, NJ). All stimulants were diluted in PBS. Mice were administered gliadin, zein (2 mg/g mouse weight), LPS (20 µg/g mouse weight), ATI (0.075 mg/g mouse weight) in 200 µl PBS. Mice were euthanized 4 hrs after gavage and the duodenum snap frozen in liquid nitrogen.

Cytokine/Chemokine Assays

The concentration of IL-8, TNF-α, MCP-1, RANTES, and mouse IL-8 (KC) in cell culture supernatants and serum samples was determined using validated ELISAs (IL-8, hTNFα: BD Pharmingen, San Jose, CA; MCP-1, hRANTES, mRANTES, KC: R&D Systems, (Minneapolis, MN; mTNFα: eBioscience, San Diego, CA), according to the manufacturer's protocols.

RNA Isolation and qRTPCR

Samples from the small intestine (0.5 cm segment, 2 cm distal to the pylorus) were collected at sacrifice and snap-frozen for further analysis. Total RNA isolation was performed using Trizol reagent (Invitrogen) according to the manufacturer's instructions. Exon-exon boundary spanning primer sequences were obtained from PrimerBank (http://pga.mgh.harvard.edu/primerbank/) and sequences are listed in Table [x]. Real-time PCR was performed using LightCycler 480 SYBR Green mastermix (Roche, Indianapolis, IN) and a Roche LightCycler 480 system. Mouse GAPDH served as endogenous control. PCR was set up in triplicates and threshold cycle (Ct) values of the target genes were normalized to the endogenous control. Differential expression was calculated according to the 2-ΔΔCT method.

Blocking Experiments

Monocyte derived dendritic cells were seeded at a concentration of 1×10⁶/ml in 96 well plates. Cells were pre-incubated with blocking antibodies (polyclonal rat anti-TLR4, Invivogen, 10 µg/ml), polyclonal goat anti-CD14, R&D, 20 µg/ml) for 3 hrs at 37° C. before stimulation.

Flow Cytometry

Human monocyte derived DC were stimulated with LPS, PT gliadin, and PT zein overnight. For flow cytometry analysis, cells were pre-incubated with FcR blocking reagent (Miltenyi) for 15 min at 4° C. before staining with monoclonal antibodies (final concentration 10 µg/ml, all from eBioscience) for 30 min at 4° C. Cells were then washed with staining buffer (PBS, 1% BSA), cell viability was assessed by DAPI exclusion (0.1 µg/ml, Roche) and only viable cells were analyzed by flow cytometry using a 4 laser LSRII (BD Biosciences) and Flowjo software (Tree Star, Inc.).

Recombinant Expression of AAI CM3 and 0.19 Proteins

Recombinant flag-tagged CM3 or 0.19 were generated in a eukaryotic system using the expression vector pCDNA (Invitrogen) and HEK 293 cells. cDNA was optimized and synthesized by genescript (sequence number AY436554.1) and correct orientation was checked by sequencing analysis. The expressed protein was purified from supernatant with anti-flag agarose beads in batch technique according to the manufacturer's protocol (Sigma).

Statistical Analysis

Differences were tested for statistical significance by the unpaired t-test. p<0.05 was considered significant. In all graphs, error bars depict standard errors of the mean.

Recombinant Expression of ATI CM3 and 0.19 Proteins

In order to exclude bacterial contaminants, recombinant flag-tagged ATI CM3 and 0.19 were generated in eukaryotic HEK-293 cells, using cDNAs optimized to fit eukaryotic codon usage (Genscript, Piscataway, NJ; CM3 and 0.19 with NCBI GenBank sequence numbers AY436554.1 and AY729672.1, respectively). cDNAs were cloned into pUC57 and correct reading frames and orientations confirmed by sequence analysis and KpnI-ApaI restriction. CM3 and 0.19 open reading frames were then cloned into pcDNA3.1 (+) (Invitrogen). In order to increase expression level of ATI 0.19, the HindIII-KpnI fragment of the PCR product was fused with the Flag-tag at the N- instead of the C-terminus using the forward primer 5'-CCCAAGCT-TAGCGGACCCTGGATGTGCTAC (SEQ ID NO: 15) and the reverse primer 5'-CGGGGTACCCCTCAGGCGTCAGGGTAAGCGGC-CAC (SEQ ID NO: 16). The CM3 and 0.19 constructs were then subcloned into the pFLAG-CMV4 vector (Sigma-Aldrich) and the correct orientation was confirmed by sequencing with the N-terminal sequencing primer 5'-AATGTCGTAATAACCCCGCCCC-GTTGACGC (SEQ ID NO: 17).

Subconfluent HEK-293 cells cultured on 10 cm tissue culture dishes were transfected with 10 µg of plasmid DNA encoding CM3 and 0.19 using lipofectamine 2000 (Invitrogen), followed by incubation in DMEM (Mediatech) containing 1% fetal bovine serum and 100 IU penicillin/100 µg/ml streptomycin for 48 h. The media were obtained by centrifugation at 4,500 rpm for 10 min at 4° C. Cells were then washed with ice cold-PBS [pH 7.4], resuspended in buffer C (20 mM Tris-HCl [pH 7.4], 150 mM NaCl, 50 mM NaF, 1 mM $Na_3VO_4$, 1 mM EDTA, 0.5% TritonX-100, 0.5% sodium deoxycholate) supplemented with EDTA-free Complete protease inhibitors (Roche) for 15 min on ice, and then centrifuged at 14,000 rpm for 20 min at 4° C. Aliquots of the detergent-soluble and insoluble fractions were boiled at 100° C. (the pellet in SDS sample buffer), separated on a SDS-15% polyacrylamide gel, and subjected to Western blot analysis. Protein lysates were probed with rabbit anti-flag antibody (Sigma-Aldrich), followed by horseradish peroxidase-labeled anti-rabbit IgG (Vector Laboratories, Burlingame, CA). Protein bands were visualized using enhanced chemiluminescence (Thermo Scientific, Rockford, IL) and X-Oat 2000A processor (Kodak).

Purification of α-Amylase Inhibitors, CM3 and 0.19

While sufficient CM3 protein was secreted into the media, 0.19 ATI had to be isolated from the detergent-soluble fraction. Briefly, HEK-cells expressing 0.19 were washed with ice cold-PBS, resuspended in 50 ml of buffer C for 15 min on ice, and centrifuged at 14,000 rpm for 20 min at 4° C. Thus, the solubilized 0.19 and soluble CM3 were bound to Flag-M2 agarose (Sigma-Aldrich) pre-equilibrated with buffer C by gentle shaking for 3 h at 4° C., washed three times with buffer C, and further washed three times with buffer D (Buffer C without detergents). Bound ATIs were eluted with TBS [pH 7.4] containing Flag peptide (Sigma-Aldrich). In order to rigorously exclude endotoxin, eluted CM3 and 0.19 were also applied to an entotoxin removal column (Norgen Biotek corp., Thorold, ON, Canada). ATIs were the used at 5 µg/ml to stimulate HEK-293 cells stably transfected with the TLR4-CD14-MD2 complex, and IL-8 secretion was quantified after 24 h using the IL-8 ELISA as described above.

Downstream Signaling Pathways Induced by CM3 and 0.19 Overexpression

HEK-293 cells stably expressing TLR4-CD14-MD2 were induced to express CM3 or 0.19, respectively, followed by cell lysis in buffer C. Lysates were cleared by centrifugation at 14,000 rpm for 20 min at 4° C., and 50 µg of protein run on a 15% SDS-gel and subjected to Western blotting to analyze activation of the canonical and the alternative (p-IRF3) pathways using antibodies to phosphorylated and unphosphorylated (p-NF-κB/p65) and IRF3 (all from Cell Signaling Technology, Danvers, MA).

Other Embodiments

Various modifications and variations of the described methods and compositions of the invention will be apparent to those skilled in the art without departing from the scope and spirit of the invention. Although the invention has been described in connection with specific desired embodiments, it should be understood that the invention as claimed should not be unduly limited to such specific embodiments. Indeed, various modifications of the described modes for carrying out the invention that are obvious to those skilled in the fields of medicine, immunology, pharmacology, endocrinology, or related fields are intended to be within the scope of the invention.

All publications mentioned in this specification are herein incorporated by reference to the same extent as if each independent publication was specifically and individually incorporated by reference.

What is claimed is:

1. A method of making a food product comprising:

a) obtaining a cereal selected from the group consisting of wheat and barley, b) reducing a level of proteins CM3 and 0.19 in the cereal by greater than 80% relative to the level of CM3 and 0.19 in a naturally occurring form of the cereal, wherein the CM3 and 0.19 in the cereal have the amino acid sequence of SEQ ID NO: 1 and 2, respectively, or variants thereof with up to 90% sequence identity thereto, and c) determining the cereal of step b) as having a reduced inflammatory activity relative to the naturally occurring form of the cereal by detecting reduced IL-8 secretion in a Toll-like Receptor 4 (TLR4) activation assay, and d) producing the food product from the cereal of step b).

2. The method of claim 1, wherein the level of CM3 and 0.19 is reduced at least 90% relative to the level of CM3 and 0.19 in the naturally occurring form of the cereal.

3. The method of claim 2, wherein the level of CM3 and 0.19 is reduced at least 95% relative to the level of CM3 and 0.19 in the naturally occurring form of the cereal.

4. The method of claim 3, wherein the level of CM3 and 0.19 is reduced at least 99% relative to the level of CM3 and 0.19 in the naturally occurring form of the cereal.

5. The method of claim 1, wherein the CM3 and 0.19 have the amino acid sequence of SEQ ID NO: 1 and 2, respectively.

* * * * *

SEQUENCE LISTING

```
<160> NUMBER OF SEQ ID NOS: 19

<210> SEQ ID NO 1
<211> LENGTH: 175
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 1

Met Ala Cys Lys Ser Ser Cys Ser Leu Leu Leu Leu Ala Ala Val Leu
1               5                   10                  15

Leu Ser Val Leu Ala Ala Ala Ser Ala Ser Gly Ser Cys Val Pro Gly
                20                  25                  30

Val Ala Phe Arg Thr Asn Leu Leu Pro His Cys Arg Asp Tyr Val Leu
            35                  40                  45

Gln Gln Thr Cys Gly Thr Phe Thr Pro Gly Ser Leu Pro Glu Trp Met
        50                  55                  60

Thr Ser Ala Ser Ile Tyr Ser Pro Gly Lys Pro Tyr Leu Ala Lys Leu
65                  70                  75                  80

Tyr Cys Cys Gln Glu Leu Ala Glu Ile Ser Gln Gln Cys Arg Cys Glu
                85                  90                  95

Ala Leu Arg Tyr Phe Ile Ala Leu Pro Val Pro Ser Gln Pro Val Asp
            100                 105                 110

Pro Arg Ser Gly Asn Val Gly Glu Ser Gly Leu Ile Asp Leu Pro Gly
        115                 120                 125

Cys Pro Arg Glu Met Gln Trp Asp Phe Val Arg Leu Leu Val Ala Pro
    130                 135                 140

Gly Gln Cys Asn Leu Ala Thr Ile His Asn Val Arg Tyr Cys Pro Ala
145                 150                 155                 160

Val Glu Gln Pro Leu Trp Ile Asp Tyr Lys Asp Asp Asp Lys
                165                 170                 175
```

```
<210> SEQ ID NO 2
<211> LENGTH: 123
<212> TYPE: PRT
<213> ORGANISM: Triticum aestivum

<400> SEQUENCE: 2
```

Ser Gly Pro Trp Met Cys Tyr Pro Gly Gln Ala Phe Gln Val Pro Ala
1               5                   10                  15

Leu Pro Ala Cys Arg Pro Leu Leu Arg Leu Gln Cys Asn Gly Ser Gln
            20                  25                  30

Val Pro Glu Ala Val Leu Arg Asp Cys Cys Gln Gln Leu Ala His Ile
        35                  40                  45

Ser Glu Trp Cys Arg Cys Gly Ala Leu Tyr Ser Met Leu Asp Ser Met
    50                  55                  60

Tyr Lys Glu His Gly Ala Gln Glu Gly Gln Ala Gly Thr Gly Ala Phe
65                  70                  75                  80

Pro Arg Cys Arg Arg Glu Val Val Lys Leu Thr Ala Ala Ser Ile Thr
                85                  90                  95

Ala Val Cys Arg Leu Pro Ile Val Val Asp Ala Ser Gly Asp Gly Ala
            100                 105                 110

Tyr Val Cys Lys Asp Val Ala Ala Tyr Pro Asp
        115                 120

```
<210> SEQ ID NO 3
<211> LENGTH: 145
<212> TYPE: PRT
<213> ORGANISM: Triticum aestivum

<400> SEQUENCE: 3
```

Met Ala Ser Lys Ser Ser Ile Ser Pro Leu Leu Leu Ala Thr Val Leu
1               5                   10                  15

Val Ser Val Phe Ala Ala Ala Thr Ala Thr Gly Pro Tyr Cys Tyr Ala
            20                  25                  30

Gly Met Gly Leu Pro Ile Asn Pro Leu Glu Gly Cys Arg Glu Tyr Val
        35                  40                  45

Ala Gln Gln Thr Cys Gly Ile Ser Ile Ser Gly Ser Ala Val Ser Thr
    50                  55                  60

Glu Pro Gly Asn Thr Pro Arg Asp Arg Cys Cys Lys Glu Leu Tyr Asp
65                  70                  75                  80

Ala Ser Gln His Cys Arg Cys Glu Ala Val Arg Tyr Phe Ile Gly Arg
                85                  90                  95

Arg Ser Asp Pro Asn Ser Ser Val Leu Lys Asp Leu Pro Gly Cys Pro
            100                 105                 110

Arg Glu Pro Gln Arg Asp Phe Ala Lys Val Leu Val Thr Ser Gly His
        115                 120                 125

Cys Asn Val Met Thr Val His Asn Ala Pro Tyr Cys Leu Gly Leu Asp
    130                 135                 140

Ile
145

```
<210> SEQ ID NO 4
<211> LENGTH: 145
<212> TYPE: PRT
<213> ORGANISM: Triticum aestivum
```

-continued

```
<400> SEQUENCE: 4

Met Ala Ser Lys Ser Ser Ile Thr His Leu Leu Ala Ala Val Leu
1               5                   10                  15

Val Ser Val Phe Ala Ala Ala Ala Thr Gly Pro Tyr Cys Tyr Pro
                20                  25                  30

Gly Met Gly Leu Pro Ser Asn Pro Leu Glu Gly Cys Arg Glu Tyr Val
            35                  40                  45

Ala Gln Gln Thr Cys Gly Val Gly Ile Val Gly Ser Pro Val Ser Thr
    50                  55                  60

Glu Pro Gly Asn Thr Pro Arg Asp Arg Cys Cys Lys Glu Leu Tyr Asp
65                  70                  75                  80

Ala Ser Gln His Cys Arg Cys Glu Ala Val Arg Tyr Phe Ile Gly Arg
                85                  90                  95

Thr Ser Asp Pro Asn Ser Gly Val Leu Lys Asp Leu Pro Gly Cys Pro
            100                 105                 110

Arg Glu Pro Gln Arg Asp Phe Ala Lys Val Leu Val Thr Pro Gly His
            115                 120                 125

Cys Asn Val Met Thr Val His Asn Thr Pro Tyr Cys Leu Gly Leu Asp
    130                 135                 140

Ile
145

<210> SEQ ID NO 5
<211> LENGTH: 145
<212> TYPE: PRT
<213> ORGANISM: Triticum aestivum

<400> SEQUENCE: 5

Met Ala Ser Lys Ser Ser Ile Thr Pro Leu Leu Ala Ala Val Leu
1               5                   10                  15

Ala Ser Val Phe Ala Ala Ala Thr Ala Thr Gly Gln Tyr Cys Tyr Ala
                20                  25                  30

Gly Met Gly Leu Pro Ser Asn Pro Leu Glu Gly Cys Arg Glu Tyr Val
            35                  40                  45

Ala Gln Gln Thr Cys Gly Val Thr Ile Ala Gly Ser Pro Val Ser Ser
    50                  55                  60

Glu Pro Gly Asp Thr Pro Lys Asp Arg Cys Cys Gln Glu Leu Asp Glu
65                  70                  75                  80

Ala Pro Gln His Cys Arg Cys Glu Ala Val Arg Tyr Phe Ile Gly Arg
                85                  90                  95

Arg Ser His Pro Asp Trp Ser Val Leu Lys Asp Leu Pro Gly Cys Pro
            100                 105                 110

Lys Glu Pro Gln Arg Asp Phe Ala Lys Val Leu Val Thr Pro Gly Gln
            115                 120                 125

Cys Asn Val Leu Thr Val His Asn Ala Pro Tyr Cys Leu Gly Leu Asp
    130                 135                 140

Ile
145

<210> SEQ ID NO 6
<211> LENGTH: 171
<212> TYPE: PRT
<213> ORGANISM: Hordeum vulgare
```

<400> SEQUENCE: 6

Met Ala Cys Lys Ser Arg Ser Leu Leu Leu Ala Thr Val Met
1               5                   10                  15

Val Ser Val Phe Ala Ala Ala Ala Ala Ala Ala Thr Asp Cys
                20                  25                  30

Ser Pro Gly Val Ala Phe Pro Thr Asn Leu Leu Gly His Cys Arg Asp
            35                  40                  45

Tyr Val Leu Gln Gln Thr Cys Ala Val Phe Thr Pro Gly Ser Lys Leu
        50                  55                  60

Pro Glu Trp Met Thr Ser Ala Glu Leu Asn Tyr Pro Gly Gln Pro Tyr
65                  70                  75                  80

Leu Ala Lys Leu Tyr Cys Cys Gln Glu Leu Ala Glu Ile Pro Gln Gln
                85                  90                  95

Cys Arg Cys Glu Ala Leu Arg Tyr Phe Met Ala Leu Pro Val Pro Ser
            100                 105                 110

Gln Pro Val Asp Pro Ser Thr Gly Asn Val Gly Gln Ser Gly Leu Met
        115                 120                 125

Asp Leu Pro Gly Cys Pro Arg Glu Met Gln Arg Asp Phe Val Arg Leu
130                 135                 140

Leu Val Ala Pro Gly Gln Cys Asn Leu Ala Thr Ile His Asn Val Arg
145                 150                 155                 160

Tyr Cys Pro Ala Val Glu Gln Pro Leu Trp Ile
                165                 170

<210> SEQ ID NO 7
<211> LENGTH: 143
<212> TYPE: PRT
<213> ORGANISM: Triticum aestivum

<400> SEQUENCE: 7

Met Ala Ser Lys Ser Asn Cys Val Leu Leu Leu Ala Ala Val Leu Val
1               5                   10                  15

Ser Ile Phe Ala Ala Val Ala Ala Ile Gly Asn Glu Asp Cys Thr Pro
                20                  25                  30

Trp Met Ser Thr Leu Ile Thr Pro Leu Pro Ser Cys Arg Asp Tyr Val
            35                  40                  45

Glu Gln Gln Ala Cys Arg Ile Glu Thr Pro Gly Ser Pro Tyr Leu Ala
        50                  55                  60

Lys Gln Gln Cys Cys Gly Glu Leu Ala Asn Ile Pro Gln Gln Cys Arg
65                  70                  75                  80

Cys Gln Ala Leu Arg Tyr Phe Met Gly Pro Lys Ser Arg Pro Asp Gln
                85                  90                  95

Ser Gly Leu Met Glu Leu Pro Gly Cys Pro Arg Glu Val Gln Met Asp
            100                 105                 110

Phe Val Arg Ile Leu Val Thr Pro Gly Tyr Cys Asn Leu Thr Thr Val
        115                 120                 125

His Asn Thr Pro Tyr Cys Leu Ala Met Glu Glu Ser Gln Trp Ser
130                 135                 140

<210> SEQ ID NO 8
<211> LENGTH: 149
<212> TYPE: PRT
<213> ORGANISM: Hordeum vulgare

<400> SEQUENCE: 8

Met Ala Ser Lys Ser Ser Cys Asp Leu Leu Ala Ala Val Leu Val
1               5                   10                  15

Ser Ile Phe Ala Ala Val Ala Ala Val Gly Ser Glu Asp Cys Thr Pro
            20                  25                  30

Trp Thr Ala Thr Pro Ile Thr Pro Leu Pro Ser Cys Arg Asp Tyr Val
            35                  40                  45

Glu Gln Gln Ala Cys Arg Ile Glu Thr Pro Gly Pro Pro Tyr Leu Ala
        50                  55                  60

Lys Gln Gln Cys Cys Gly Glu Leu Ala Asn Ile Pro Gln Gln Cys Arg
65                  70                  75                  80

Cys Gln Ala Leu Arg Phe Phe Met Gly Arg Lys Ser Arg Pro Asp Gln
                85                  90                  95

Ser Gly Leu Met Glu Leu Pro Gly Cys Pro Arg Glu Val Gln Met Asp
            100                 105                 110

Phe Val Arg Ile Leu Val Thr Pro Gly Phe Cys Asn Leu Thr Thr Val
        115                 120                 125

His Asn Thr Pro Tyr Cys Leu Ala Met Asp Glu Trp Gln Trp Asn Arg
    130                 135                 140

Gln Phe Cys Ser Ser
145

<210> SEQ ID NO 9
<211> LENGTH: 121
<212> TYPE: PRT
<213> ORGANISM: Triticum aestivum

<400> SEQUENCE: 9

Met Ala Phe Lys His Gln Leu Ile Leu Ser Thr Ala Ile Leu Leu Ala
1               5                   10                  15

Val Leu Ala Ala Ala Ser Ala Ser Phe Arg Glu Gln Cys Val Pro Gly
            20                  25                  30

Arg Glu Ile Thr Tyr Glu Ser Leu Asn Ala Arg Arg Glu Tyr Ala Val
            35                  40                  45

Arg Gln Thr Cys Gly Tyr Tyr Leu Ser Ala Glu Arg Gln Lys Arg Arg
        50                  55                  60

Cys Cys Asp Glu Leu Ser Lys Val Pro Glu Leu Cys Trp Cys Glu Val
65                  70                  75                  80

Leu Arg Ile Leu Met Asp Arg Arg Val Thr Lys Glu Gly Val Val Lys
                85                  90                  95

Gly Ser Leu Leu Gln Asp Met Ser Arg Cys Lys Lys Leu Thr Arg Glu
            100                 105                 110

Phe Ile Ala Gly Ile Val Gly Arg Glu
        115                 120

<210> SEQ ID NO 10
<211> LENGTH: 121
<212> TYPE: PRT
<213> ORGANISM: Triticum aestivum

<400> SEQUENCE: 10

Met Ala Phe Lys His Gln Leu Ile Leu Ser Thr Ala Ile Leu Leu Ala
1               5                   10                  15

Val Leu Ala Ala Ala Ser Ala Ser Phe Arg Glu Gln Cys Val Pro Gly
            20                  25                  30

```
Arg Glu Ile Thr Tyr Glu Ser Leu Asn Ala Arg Glu Tyr Ala Val
                35                  40                  45

Arg Gln Thr Cys Gly Tyr Tyr Leu Ser Ala Glu Arg Gln Lys Arg Arg
 50                      55                  60

Cys Cys Asp Glu Leu Ser Lys Val Pro Glu Leu Cys Trp Cys Glu Val
 65                  70                  75                  80

Leu Arg Ile Leu Met Asp Arg Arg Val Thr Lys Glu Gly Val Val Lys
                 85                  90                  95

Asp Ser Leu Leu Gln Asp Met Ser Arg Cys Lys Lys Leu Thr Arg Glu
                100                 105                 110

Phe Ile Ala Gly Ile Val Gly Arg Glu
            115                 120

<210> SEQ ID NO 11
<211> LENGTH: 124
<212> TYPE: PRT
<213> ORGANISM: Triticum aestivum

<400> SEQUENCE: 11

Ser Gly Pro Trp Met Cys Tyr Pro Gly Gln Ala Phe Gln Val Pro Ala
 1               5                  10                  15

Leu Pro Gly Cys Arg Pro Leu Leu Lys Leu Gln Cys Asn Gly Ser Gln
                 20                  25                  30

Val Pro Glu Ala Val Leu Arg Asp Cys Cys Gln Gln Leu Ala Asp Ile
                 35                  40                  45

Ser Glu Trp Pro Arg Cys Gly Ala Leu Tyr Ser Met Leu Asp Ser Met
 50                      55                  60

Tyr Lys Glu His Gly Val Ser Glu Gly Gln Ala Gly Thr Gly Ala Phe
 65                  70                  75                  80

Pro Ser Cys Arg Arg Glu Val Val Lys Leu Thr Ala Ala Ser Ile Thr
                 85                  90                  95

Ala Val Cys Arg Leu Pro Ile Val Val Asp Ala Ser Gly Asp Gly Ala
                100                 105                 110

Tyr Val Cys Lys Asp Val Ala Ala Tyr Pro Asp Ala
            115                 120

<210> SEQ ID NO 12
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 12

Cys Ser Lys Lys Lys Lys
 1               5

<210> SEQ ID NO 13
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 13

Leu Gly Gln Gln Gln Pro Phe Pro Pro Gln Gln Pro Tyr
 1               5                  10
```

```
<210> SEQ ID NO 14
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 14

Gly Leu Gln Pro Phe Gln Gln Pro Gln Pro Pro Gln Tyr
1               5                   10

<210> SEQ ID NO 15
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 15
cccaagctta gcggaccctg gatgtgctac                                     30

<210> SEQ ID NO 16
<211> LENGTH: 35
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 16
cggggtaccc ctcaggcgtc agggtaagcg gccac                               35

<210> SEQ ID NO 17
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 17
aatgtcgtaa taaccccgcc ccgttgacgc                                     30

<210> SEQ ID NO 18
<211> LENGTH: 168
<212> TYPE: PRT
<213> ORGANISM: Triticum aestivum

<400> SEQUENCE: 18

Met Ala Cys Lys Ser Ser Cys Ser Leu Leu Leu Ala Ala Val Leu
1               5                   10                  15

Leu Ser Val Leu Ala Ala Ala Ser Ala Ser Gly Ser Cys Val Pro Gly
                20                  25                  30

Val Ala Phe Arg Thr Asn Leu Leu Pro His Cys Arg Asp Tyr Val Leu
        35                  40                  45

Gln Gln Thr Cys Gly Thr Phe Thr Pro Gly Ser Lys Leu Pro Glu Trp
    50                  55                  60

Met Thr Ser Ala Ser Ile Tyr Ser Pro Gly Lys Pro Tyr Leu Ala Lys
65                  70                  75                  80

Leu Tyr Cys Cys Gln Glu Leu Ala Glu Ile Ser Gln Gln Cys Arg Cys
                85                  90                  95
```

-continued

```
Glu Ala Leu Arg Tyr Phe Ile Ala Leu Pro Val Pro Ser Gln Pro Val
            100                 105                 110

Asp Pro Arg Ser Gly Asn Val Gly Glu Ser Gly Leu Ile Asp Leu Pro
        115                 120                 125

Gly Cys Pro Arg Glu Met Gln Trp Asp Phe Val Arg Leu Leu Val Ala
    130                 135                 140

Pro Gly Gln Cys Asn Leu Ala Thr Ile His Asn Val Arg Tyr Cys Pro
145                 150                 155                 160

Ala Val Glu Gln Pro Leu Trp Ile
                165

<210> SEQ ID NO 19
<211> LENGTH: 124
<212> TYPE: PRT
<213> ORGANISM: Triticum aestivum

<400> SEQUENCE: 19

Ser Gly Pro Trp Met Cys Tyr Pro Gly Gln Ala Phe Gln Val Pro Ala
1               5                   10                  15

Leu Pro Ala Cys Arg Pro Leu Leu Arg Leu Gln Cys Asn Gly Ser Gln
            20                  25                  30

Val Pro Glu Ala Val Leu Arg Asp Cys Cys Gln Gln Leu Ala His Ile
        35                  40                  45

Ser Glu Trp Cys Arg Cys Gly Ala Leu Tyr Ser Met Leu Asp Ser Met
    50                  55                  60

Tyr Lys Glu His Gly Ala Gln Glu Gly Gln Ala Gly Thr Gly Ala Phe
65                  70                  75                  80

Pro Arg Cys Arg Arg Glu Val Val Lys Leu Thr Ala Ala Ser Ile Thr
                85                  90                  95

Ala Val Cys Arg Leu Pro Ile Val Val Asp Ala Ser Gly Asp Gly Ala
            100                 105                 110

Tyr Val Cys Lys Asp Val Ala Ala Tyr Pro Asp Ala
        115                 120
```